(12) United States Patent
Beraud et al.

(10) Patent No.: US 6,794,178 B2
(45) Date of Patent: Sep. 21, 2004

(54) KINI-3 MOTOR PROTEIN AND METHODS FOR ITS USE

(75) Inventors: Christophe Beraud, Palm Springs, CA (US); Jun Guo, Fremont, CA (US); Richard Freedman, San Mateo, CA (US); Umesh A. Patel, Cambridge (GB); Katherine A. Davies, Cambridge (GB)

(73) Assignee: Cytokinetics, South San Francisco, CA (US)

( * ) Notice: Subject to any disclaimer, the term of this patent is extended or adjusted under 35 U.S.C. 154(b) by 17 days.

(21) Appl. No.: 10/159,151

(22) Filed: May 31, 2002

(65) Prior Publication Data

US 2003/0036075 A1 Feb. 20, 2003

Related U.S. Application Data

(60) Division of application No. 09/967,908, filed on Sep. 28, 2001, now Pat. No. 6,514,738, which is a continuation-in-part of application No. 09/675,227, filed on Sep. 29, 2000, now Pat. No. 6,461,855.

(51) Int. Cl.[7] ............................ C12N 1/20; C12N 9/16; C12N 15/00; C07H 21/04; C12Q 1/44
(52) U.S. Cl. ................. 435/252.3; 435/196; 435/320.1; 435/19; 536/23.2
(58) Field of Search .............................. 435/252.3, 196, 435/320.1, 19; 536/23.2

(56) References Cited

FOREIGN PATENT DOCUMENTS

WO    WO 99/53295    10/1999

OTHER PUBLICATIONS

Bray–Allen, "Homo Sapiens Chromosome 9 clone RP11–571F15, *Sequencing in Progress*, 81 unordered places," GenBank ID No. AL353661, 139 pages.

Miller et al, "Kinesin homolog (*Monodelphis demostica*)", GenBank ID No. AAB62895, 2 pages.

Miller, et al., "*Monodelphis domestica* kinesin homolog mRNA, partial CDS," GenBank ID No. AF005901, 2 pages.

Neto et al., "Shotgun sequencing of the human Transcription with ORF expressed sequence tags," PNAS, (97):3491–3496 (2000).

Wordeman et al, "Identification and Partial Characterization of Mitotic Centromere–associated Kinesin, a Kinesin–related Protein that associates with Centromeres during Mitosis," J. Cell Biol., 128(1–2):95–105 (1995).

*Primary Examiner*—Tekchand Saidha
(74) *Attorney, Agent, or Firm*—Townsend and Townsend and Crew

(57) ABSTRACT

The invention provides isolated nucleic acid and amino acid sequences of KinI-3, antibodies to KinI-3, methods of screening for KinI-3 modulators using biologically active KinI-3, and kits for screening for KinI-3 modulators.

12 Claims, 11 Drawing Sheets

KinI-3 nucleotide sequence (SEQ ID NO:1)

Start codon ATG
Stop codon TAG
Motor domain

```
gcggccgcgaattcggcacgaggctggccgccgccggtggctcccgggttgacgggact
gttaggttgcgggctttggggctcactcccgacggcattgtcttctcctcttctcagac
agggcagaccgaggagtttggaccgagagtttatagaaacctattcaccaaaatggcat
cctggttatatgaatgtctttgtgaagctgaacttgcacagtattattctcatttcact
gcccttggccttcagaaaatagatgaattagccaagattacaatgaaggactactccaa
attaggagtccatgacatgaacgaccgcaaacgtctcttccaacttatcaaaattatta
agattatgcaagaagaagataaagcagtcagtatcccagagcgtcatcttcagacaagc
agcctgcgcatcaaatctcaggaattaagatctggccctcgcagacagctgaattttga
ttctcctgctgacaataaagacagaaatgccagcaatgatgggtttgaaatgtgcagtt
tatcagatttctctgcaaatgaacagaagtccacttacctaaaagtgctagaacacatg
ctaccagatgattcccagtaccatacaaaaacaggaattctgaatgccacagctggtga
ttcctatgtgcaaacagaaatcagcacttcactcttttcaccaaattacctttctgcaa
tactgggggattgtgatattcccattattcaaagaatctctcatgtttcagggtataac
tatggaatccctcattcttgtatcagacagaacacttcagagaaacagaatccttggac
tgagatggagaaaatcagagtttgtgttcgaaaacgcccctgggcatgagggaggtac
gtcgtggagaaattaatattattactgtagaagacaaagaaactctacttgtgcatgag
aagaaagaagcagttgacctcactcaatatattctgcagcatgttttttattttgatga
agtctttggtgaggcgtgcaccaatcaggatgtatacatgaagactactcacccactta
ttcagcatatttcaatggaggcaatgccacttgctttgcttatggacagacaggtgct
ggaaagacctacaccatgataggaactcatgagaacccaggattgtatgctctagctgc
caaagatatcttcaggcaactagaagtgtcccagccaagaaagcacctctttgtgtgga
tcagcttctatgaaatttactgtggacagctttatgacctcctaaatagaagaaaaagg
ctctttgcaagagaagatagcaagcacatggtgcagatagtgggactgcaagagcttca
ggtggacagtgtggagctcctcttagaggtgatcttaaagggcagcaaggagcgcagca
ctggggccactggagttaatgcagactcctcccgctcccatgccgtcatccaaattcag
atcaaagattcagccaagaggacatttggcaggatctcttttattgacttggctggcag
tgaaagagcagcagatgcaagggactcagatagacagacaaagatggaaggtgcagaaa
taaatcagagtctactggctctgaaggaatgtatccgagcactggatcaggaacacacc
catactccccttcaggcaaagcaaactaactcaggtcctgaaggactctttcatcggcaa
tgccaaaacctgcatgatcgccaacatctcaccaagccacgtggccactgaacacactc
tcaacaccttgcgctatgctgaccgggtcaaagaactaaagaaaggcattaagtgttgc
acttcagttaccagtcgaaatcggacatctggaaactcctctccaaaacgaattcagag
ctcccctgggcgtttgtcagaggacaaatgttctcccaaaaagtcaagctggatttc
agcagtcactcacagtggcagccctggttccacgagagggaaggtccatcctctgacc
agccacccacccaacattccttttacttctgcacctaaggtctctggtaaaaggggtgg
ctccagagggagtccttcacaagagtgggtcattcatgctagccctgtgaaaggaactg
tgcgctctggacatgtggccaaaaaaagccagaagagtcagcaccattgtgctctgag
aaaaatcgaatgggcaacaaaactgtccttgggtgggaaagcagggcctcaggcccagg
agaaggcctagtgcgtggtaagctgtccaccaagtgcaagaaagtgcagacagtgcagc
cagtacagaagcagcttgtgtctcgagttgagctctcctttggcaacgcccaccacagg
gctgagtacagtcaagacagccagaggggcacgcctgctaggcctgcctctgaagcttg
```

FIG. 1A

```
gacaaacatcccgccacatcagaaggagagggaggaacatctgcgtttctatcaccagc
agttccaacagccacctctcctccaacagaagttaaaataccaaccactgaaaaggtct
ttacgccagtacaggcccccagagggtcagctcacgaatgagactccgcctctgttcca
ctcttactctgaaaaccatgatggagcccaagtagaggaacttgatgacagtgatttca
gtgaagattcttttttcacacatctctagtcagagggccacaaagcaaaggaacaccctg
gagaatagcgaagactcattcttcctgcaccagacgtggggacagggtcctgagaagca
ggtggcagaaagacagcagagtctgttttctagccccaggacaggtgacaagaaagatc
taactaaaagctgggtggactccagggaccccataaaccacagaagagcagcactcgat
cacagctgcagcccaagtaaggggcccgtggactggagcagagagaactctacttcctc
agggccttctcccagagacagcctggcagagaagccatactgttcacaggtagatttca
tatatagacaggaaagaggtggaggctcttcctttgatctcagaaaggatgcctcccaa
agtgaggtttctggggagaatgagggcaacttgccatccccagaggaagatggtttcac
tatctcattgtcccacgttgcagttcctggatccccagaccaaagagacacagtcacca
cacctctgagagaagtcagtgcagacggcccaatccaggtgaccagcactgtgaaaaac
ggtcatgctgtcccaggagaggatcctagggggcagttaggcacgcatgctgaatatgc
ttctggactcatgtctcccctcaccatgtccctcctggagaacccagacaacgaagggt
ctcctccctcggagcagctggtccaggatggggctacgcacagtctagtggcagagagc
acaggggcccagttgtgagccacacagtgccatctggtgatcaagaggcagccttgcc
agtgtcttcagcaactaggcacctgtggctgtcctcatctcccctgataataagcctg
gtggtgatcttccagctctgtccccatcacccatccgtcagcacccagctgacaagctg
cccagcagggaggcagacctaggagaggcctgccagagcagagagactgtacttttctc
ccacgaacacatgggtagtgagcagtatgatgctgatgcagaggagacggggctggatg
gctcctggggtttcccaggaaagcccttcaccaccatacatatgggggtaccccattct
ggacctacactcaccccacgaacaggaagtagtgatgtggctgaccagctctgggccca
ggagagaaaacatcctacaaggcttggttggcaggagtttggtttgtccacagaccca
tcaagttgccctgcaacagtgaaaatgtcacatggctcaaacccaggccgatctcaagg
tgcttagcaaggccaagttctcccttggttcccagctgctctcccaagactgcagggac
actccgtcagcccaccctggagcaagcgcagcaggtggtcatccgagcacaccaggaac
agctggatgaaatggctgagctcggcttcaaggaggagacgctgatgagccagctggct
tctaatgattttgaagattttgtgacccagctggatgaaatcatggttctgaaatccaa
gtgtatccagagtctgaggagccagctgcagctctatctcacctgccacgggcccaccg
cagcccctgagggaacagtgccgtcttagagccagacctgtgccgagatggtgggggc
cctgcaggagtctgtgctggctctcaggctggaggagcctctgccaggtcctccctgc
acaccagaacccacacgctggtcctgcctatgctagcgtcaccccagccccacgtgg
cttcagataggtcccagcttctcccttcagggacaggcccctgtccctcagttccatgca
caggagtgcctccaagggtgggccaggccgaagaacctaatgcctttcccttgtgccta
gagaatatgattaactaacccccttgcctgtggggaatatatttgggtctaataaccctga
agtttctaagtttggggatcagaggatggggtggtcagtggtagcctagaggtcagagg
tcacaagacagagaagacaacatgctgagaccagaggcttcaccagctgaattctgtgc
ctaacttagaagactaaacactggcccaaacttaaccattggtgctaggggggacagggg
tggggtgagctctgcccatcagcccttggagattgatttggggatttagaggcgtttt
tgaaaatgtaaatagcataaaccttgacttgatgtgtcactgacagcagcagatgtgag
acaggccttatatttacagctccctttccttcctgcaatccagtgttgaggcagaagag
ggtgcctgtgtcacacatcaatttttctcctgacttttgctcgggtgaaaggcctctgt
```

FIG. 1B

```
acaatgcccgatactctcatgcttccatggcagctcctggctcctatctgggacacctc
actacccagcccctcatggaatagtccatctcctagcctggccttcatccagttcacc
ctgcccagccaccctgcctctcaggggtctgtgttgggaaccttggcagttgaacagag
tgctctgttcaacagtctgaggcctctgaaacagaattcacacacaaaccttcagccaa
gttctgcctgctgtgtatcttttagcaggaagcagctcaggacagggaagacaaagta
gcctccaggtgccaattactttaaagccactctgggtcaaatggagattcatgagtcac
ggccttggcccgaacgcccattactatgtgagcctttatttccttcagataaaggataa
cttttacggttttaaaaggagggcttaattaaaaggccaagaagagggttaaatggct
ctcttgagacactagcagcctggtccagtcacccttgtcagcctgacagtgcctcatc
tgaccgccagggggcatccttattggtgcttccggctgcagggcactgcggcccctcc
ctcacatgatcactaaaaaccttcaaagacccagtctagccaaaagctcaagtgggaca
atggcacagtattaaggtcaaggacaaaaacttacttactttaggaatgaaccctattc
tatcatcatatacaacagcaccactgagagctggtgaaacagtttaaatcccatcctct
gcttgtggcaaatgatgcataaatgcctgctgctcacagtaaaagggcttcttcctctt
ttactgggtgatcccctgaaggcccagcctatcccaactccacagtcaggaaggccta
cgtccttggtccacagacggagctgggccaggtttaaaagactcagtctaggcttgcct
ttgcaaaccaaaaacgaggacaggtctgaagtgggaagaaagctccgaaatagaaacg
gttaggtcctattctatccccagcaaatctaagcaagaaatctctttatacaccacatg
gcccccccactcccataaaacagccttggtaataaagaagttatcacaccaagacatac
cttttagatttttattagtagttctctctgaagaatcaaaatagttagttagcaaatta
ttttagattcaagactgtatatcctttgtatttagatctttaatgatgtacaacataat
acaaaacaaaccagagagactgatttctaaaaaaaaaaaaaaaaaaaaaaaaaaaaaa
aaaaaaaaaaaaaaaaaaaaaaaaaaaaaaaaaaaaaaaaaaaaaaaaaaaaaaaaaa
aaaaaaaaaaaaaaaaaaaaaaaaaaaaaaaaa
```

FIG. 1C

KinI-3 amino-acid sequence (SEQ ID NO:2)

Motor domain

MASWLYECLCEAELAQYYSHFTALGLQKIDELAKITMKDYSKLGVHDMNDFYFLFQLIK
IIKIMQEEDKAVSIPERHLQTSSLRIKSQELRSGPRRQLNFDSPADNKDRNAENDGFEM
CSLSDFSANEQKSTYLKVLEHMLPDDSQYHTKTGILNATAGDSYVQTEISTSLFSPNYL
SAILGDCDIPIIQRISHVSGYNYGIPHSCIRQNTSEKQNPWTEMEKIRVCVRKRPLGMR
EVRRGEINIITVEDKETLLVHEKKEAVDLTQYILQHVFYFDEVFGEACTNQDVYMKTTH
PLIQHIFNGGNATCFAYGQTGAGKTYTMIGTHENPGLYALAAKDIFRQLEVSQPRKHLF
VWISFYEIYCGQLYDLLNRRKRLFAREDSKHMVQIVGLQELQVDSVELLLEVILKGSKE
RSTGATGVNADSSRSHAVIQIQIKDSAKRTFGRISFIDLAGSERAADARDSDRQTKMEG
AEINQSLLALKECIRALDQEHTHTPFRQSKLTQVLKDSFIGNAKTCMIANISPSHVATE
HTLNTLRYADRVKELKKGIKCCTSVTSRNRTSGNSSPKRIQSSPGALSEDKCSPKKVKL
GFQQSLTVAAPGSTRGKVHPLTSHPPNIPFTSAPKVSGKRGGSRGSPSQEWVIHASPVK
GTVRSGHVAKKKPEESAPLCSEKNRMGNKTVLGWESRASGPGEGLVRGKLSTKCKKVQT
VQPVQKQLVSRVELSFGNAHHRAEYSQDSQRGTPARPASEAWTNIPPHQKEREEHLRFY
HQQFQQPPLLQQKLKYQPLKRSLRQYRPPEGQLTNETPPLFHSYSENHDGAQVEELDDS
DFSEDSFSHISSQRATKQRNTLENSEDSFFLHQTWGQGPEKQVAERQQSLFSSPRTGDK
KDLTKSWVDSRDPINHRRAALDHSCSPSKGPVDWSRENSTSSGPSPRDSLAEKPYCSQV
DFIYRQERGGGSSFDLRKDASQSEVSGENEGNLPSPEEDGFTISLSHVAVPGSPDQRDT
VTTPLREVSADGPIQVTSTVKNGHAVPGEDPRGQLGTHAEYASGLMSPLTMSLLENPDN
EGSPPSEQLVQDGATHSLVAESTGGPVVSHTVPSGDQEAALPVSSATRHLWLSSSPPDN
KPGGDLPALSPSPIRQHPADKLPSREADLGEACQSRETVLFSHEHMGSEQYDADAEETG
LDGSWGFPGKPFTTIHMGVPHSGPTLTPRTGSSDVADQLWAQERKHPTRLGWQEFGLST
DPIKLPCNSENVTWLKPRPISRCLARPSSPLVPSCSPKTAGTLRQPTLEQAQQVVIRAH
QEQLDEMAELGFKEETLMSQLASNDFEDFVTQLDEIMVLKSKCIQSLRSQLQLYLTCHG
PTAAPEGTVPS

FIG. 2

KINI-3 D183 L546

Bold type is from pET23d vector (SEQ ID NO:3)
ATGGATTGTGATATTCCCATTATTCAAAGAATCTCTCATGTTTCAGGGTATAACTATGG
AATCCCTCATTCTTGTATCAGACAGAACACTTCAGAGAAACAGAATCCTTGGACTGAGA
TGGAGAAAATCAGAGTTTGTGTTCGAAAACGCCCCTGGGCATGAGGGAGGTACGTCGT
GGAGAAATTAATATTATTACTGTAGAAGACAAAGAAACTCTACTTGTGCATGAGAAGAA
AGAAGCAGTTGACCTCACTCAATATATTCTGCAGCATGTTTTTATTTTGATGAAGTCT
TTGGTGAGGCGTGCACCAATCAGGATGTATACATGAAGACTACTCACCCACTTATTCAG
CATATTTTCAATGGAGGCAATGCCACTTGCTTTGCTTATGGACAGACAGGTGCTGGAAA
GACCTACACCATGATAGGAACTCATGAGAACCCAGGATTGTATGCTCTAGCTGCCAAAG
ATATCTTCAGGCAACTAGAAGTGTCCCAGCCAAGAAAGCACCTCTTTGTGTGGATCAGC
TTCTATGAAATTTACTGTGGACAGCTTTATGACCTCCTAAATAGAAGAAAAAGGCTCTT
TGCAAGAGAAGATAGCAAGCACATGGTGCAGATAGTGGGACTGCAAGAGCTTCAGGTGG
ACAGTGTGGAGCTCCTCTTAGAGGTGATCTTAAAGGGCAGCAAGGAGCGCAGCACTGGG
GCCACTGGAGTTAATGCAGACTCCTCCCGCTCCCATGCCGTCATCCAAATTCAGATCAA
AGATTCAGCCAAGAGGACATTTGGCAGGATCTCTTTTATTGACTTGGCTGGCAGTGAAA
GAGCAGCAGATGCAAGGGACTCAGATAGACAGACAAAGATGGAAGGTGCAGAAATAAAT
CAGAGTCTACTGGCTCTGAAGGAATGTATCCGAGCACTGGATCAGGAACACACCCATAC
TCCCTTCAGGCAAAGCAAACTAACTCAGGTCCTGAAGGACTCTTTCATCGGCAATGCCA
AAACCTGCATGATCGCCAACATCTCACCAAGCCACGTGGCCACTGAACACACTCTCAAC
ACCTTGCGCTATGCTGACCGGGTCAAAGAACTA**CTCGAGCAC CACCACCACC
ACCACTGA**

SEQ ID NO:4
MDCDIPIIQRISHVSGYNYGIPHSCIRQNTSEKQNPWTEMEKIRVCVRKRPLGMREVRR
GEINIITVEDKETLLVHEKKEAVDLTQYILQHVFYFDEVFGEACTNQDVYMKTTHPLIQ
HIFNGGNATCFAYGQTGAGKTYTMIGTHENPGLYALAAKDIFRQLEVSQPRKHLFVWIS
FYEIYCGQLYDLLNRRKRLFAREDSKHMVQIVGLQELQVDSVELLLEVILKGSKERSTG
ATGVNADSSRSHAVIQIQIKDSAKRTFGRISFIDLAGSERAADARDSDRQTKMEGAEIN
QSLLALKECIRALDQEHTHTPFRQSKLTQVLKDSFIGNAKTCMIANISPSHVATEHTLN
TLRYADRVKELLEHHHHHH*

FIG. 3

KINI-3 V195S566

SEQ ID NO:5
ATGGTTTCAGGGTATAACTATGGAATCCCTCATTCTTGTATCAGACAGAACACTTCAGA
GAAACAGAATCCTTGGACTGAGATGGAGAAAATCAGAGTTTGTGTTCGAAAACGCCCCC
TGGGCATGAGGGAGGTACGTCGTGGAGAAATTAATATTATTACTGTAGAAGACAAAGAA
ACTCTACTTGTGCATGAGAAGAAAGAAGCAGTTGACCTCACTCAATATATTCTGCAGCA
TGTTTTTTATTTTGATGAAGTCTTTGGTGAGGCGTGCACCAATCAGGATGTATACATGA
AGACTACTCACCCACTTATTCAGCATATTTTCAATGGAGGCAATGCCACTTGCTTTGCT
TATGGACAGACAGGTGCTGGAAAGACCTACACCATGATAGGAACTCATGAGAACCCAGG
ATTGTATGCTCTAGCTGCCAAAGATATCTTCAGGCAACTAGAAGTGTCCCAGCCAAGAA
AGCACCTCTTTGTGTGGATCAGCTTCTATGAAATTTACTGTGGACAGCTTTATGACCTC
CTAAATAGAAGAAAAAGGCTCTTTGCAAGAGAAGATAGCAAGCACATGGTGCAGATAGT
GGGACTGCAAGAGCTTCAGGTGGACAGTGTGGAGCTCCTCTTAGAGGTGATCTTAAAGG
GCAGCAAGGAGCGCAGCACTGGGGCCACTGGAGTTAATGCAGACTCCTCCCGCTCCCAT
GCCGTCATCCAAATTCAGATCAAAGATTCAGCCAAGAGGACATTTGGCAGGATCTCTTT
TATTGACTTGGCTGGCAGTGAAAGAGCAGCAGATGCAAGGGACTCAGATAGACAGACAA
AGATGGAAGGTGCAGAAATAAATCAGAGTCTACTGGCTCTGAAGGAATGTATCCGAGCA
CTGGATCAGGAACACACCCATACTCCCTTCAGGCAAAGCAAACTAACTCAGGTCCTGAA
GGACTCTTTCATCGGCAATGCCAAAACCTGCATGATCGCCAACATCTCACCAAGCCACG
TGGCCACTGAACACACTCTCAACACCTTGCGCTATGCTGACCGGGTCAAAGAACTAAAG
AAAGGCATTAAGTGTTGCACTTCAGTTACCAGTCGAAATCGGACATCTGGAAACTCCCT
CGAGCAC CACCACCACC ACCACTGA

SEQ ID NO:6
MVSGYNYGIPHSCIRQNTSEKQNPWTEMEKIRVCVRKRPLGMREVRRGEINIITVEDKE
TLLVHEKKEAVDLTQYILQHVFYFDEVFGEACTNQDVYMKTTHPLIQHIFNGGNATCFA
YGQTGAGKTYTMIGTHENPGLYALAAKDIFRQLEVSQPRKHLFVWISFYEIYCGQLYDL
LNRRKRLFAREDSKHMVQIVGLQELQVDSVELLLEVILKGSKERSTGATGVNADSSRSH
AVIQIQIKDSAKRTFGRISFIDLAGSERAADARDSDRQTKMEGAEINQSLLALKECIRA
LDQEHTHTPFRQSKLTQVLKDSFIGNAKTCMIANISPSHVATEHTLNTLRYADRVKELK
KGIKCCTSVTSRNRTSGNSLEHHHHHH\*

FIG. 4

KINI-3 E213L546

SEQ ID NO:7
ATGGAGAAACAGAATCCTTGGACTGAGATGGAGAAAATCAGAGTTTGTGTTCGAAAACG
CCCCCTGGGCATGAGGGAGGTACGTCGTGGAGAAATTAATATTATTACTGTAGAAGACA
AAGAAACTCTACTTGTGCATGAGAAGAAAGAAGCAGTTGACCTCACTCAATATATTCTG
CAGCATGTTTTTTATTTTGATGAAGTCTTTGGTGAGGCGTGCACCAATCAGGATGTATA
CATGAAGACTACTCACCCACTTATTCAGCATATTTTCAATGGAGGCAATGCCACTTGCT
TTGCTTATGGACAGACAGGTGCTGGAAAGACCTACACCATGATAGGAACTCATGAGAAC
CCAGGATTGTATGCTCTAGCTGCCAAAGATATCTTCAGGCAACTAGAAGTGTCCCAGCC
AAGAAAGCACCTCTTTGTGTGGATCAGCTTCTATGAATTTACTGTGGACAGCTTTATG
ACCTCCTAAATAGAAGAAAAAGGCTCTTTGCAAGAGAAGATAGCAAGCACATGGTGCAG
ATAGTGGGACTGCAAGAGCTTCAGGTGGACAGTGTGGAGCTCCTCTTAGAGGTGATCTT
AAAGGGCAGCAAGGAGCGCAGCACTGGGGCCACTGGAGTTAATGCAGACTCCTCCCGCT
CCCATGCCGTCATCCAAATTCAGATCAAAGATTCAGCCAAGAGGACATTTGGCAGGATC
TCTTTTATTGACTTGGCTGGCAGTGAAAGAGCAGCAGATGCAAGGGACTCAGATAGACA
GACAAAGATGGAAGGTGCAGAAATAAATCAGAGTCTACTGGCTCTGAAGGAATGTATCC
GAGCACTGGATCAGGAACACACCCATACTCCCTTCAGGCAAAGCAAACTAACTCAGGTC
CTGAAGGACTCTTTCATCGGCAATGCCAAAACCTGCATGATCGCCAACATCTCACCAAG
CCACGTGGCCACTGAACACACTCTCAACACCTTGCGCTATGCTGACCGGGTCAAAGAAC
TACTCGAGCAC CACCACCACC ACCACTGA

SEQ ID NO:8
MEKQNPWTEMEKIRVCVRKRPLGMREVRRGEINIITVEDKETLLVHEKKEAVDLTQYIL
QHVFYFDEVFGEACTNQDVYMKTTHPLIQHIFNGGNATCFAYGQTGAGKTYTMIGTHEN
PGLYALAAKDIFRQLEVSQPRKHLFVWISFYEIYCGQLYDLLNRRKRLFAREDSKHMVQ
IVGLQELQVDSVELLLEVILKGSKERSTGATGVNADSSRSHAVIQIQIKDSAKRTFGRI
SFIDLAGSERAADARDSDRQTKMEGAEINQSLLALKECIRALDQEHTHTPFRQSKLTQV
LKDSFIGNAKTCMIANISPSHVATEHTLNTLRYADRVKELLEHHHHHH*

FIG. 5

KINI-3 E213S566

SEQ ID NO:9
ATGGAGAAACAGAATCCTTGGACTGAGATGGAGAAAATCAGAGTTTGTGTTCGAAAACG
CCCCCTGGGCATGAGGGAGGTACGTCGTGGAGAAATTAATATTATTACTGTAGAAGACA
AAGAAACTCTACTTGTGCATGAGAAGAAAGAAGCAGTTGACCTCACTCAATATATTCTG
CAGCATGTTTTTTATTTTGATGAAGTCTTTGGTGAGGCGTGCACCAATCAGGATGTATA
CATGAAGACTACTCACCCACTTATTCAGCATATTTTCAATGGAGGCAATGCCACTTGCT
TTGCTTATGGACAGACAGGTGCTGGAAGACCTACACCATGATAGGAACTCATGAGAAC
CCAGGATTGTATGCTCTAGCTGCCAAAGATATCTTCAGGCAACTAGAAGTGTCCCAGCC
AAGAAAGCACCTCTTTGTGTGGATCAGCTTCTATGAAATTTACTGTGGACAGCTTTATG
ACCTCCTAAATAGAAGAAAAAGGCTCTTTGCAAGAGAAGATAGCAAGCACATGGTGCAG
ATAGTGGGACTGCAAGAGCTTCAGGTGGACAGTGTGGAGCTCCTCTTAGAGGTGATCTT
AAAGGGCAGCAAGGAGCGCAGCACTGGGGCCACTGGAGTTAATGCAGACTCCTCCCGCT
CCCATGCCGTCATCCAAATTCAGATCAAAGATTCAGCCAAGAGGACATTTGGCAGGATC
TCTTTTATTGACTTGGCTGGCAGTGAAAGAGCAGCAGATGCAAGGGACTCAGATAGACA
GACAAAGATGGAAGGTGCAGAAATAAATCAGAGTCTACTGGCTCTGAAGGAATGTATCC
GAGCACTGGATCAGGAACACACCCATACTCCCTTCAGGCAAAGCAAACTAACTCAGGTC
CTGAAGGACTCTTTCATCGGCAATGCCAAAACCTGCATGATCGCCAACATCTCACCAAG
CCACGTGGCCACTGAACACACTCTCAACACCTTGCGCTATGCTGACCGGGTCAAAGAAC
TAAAGAAAGGCATTAAGTGTTGCACTTCAGTTACCAGTCGAAATCGGACATCTGGAAAC
TCCCTCGAGCAC CACCACCACC ACCACTGA

SEQ ID NO:10
MEKQNPWTEMEKIRVCVRKRPLGMREVRRGEINIITVEDKETLLVHEKKEAVDLTQYIL
QHVFYFDEVFGEACTNQDVYMKTTHPLIQHIFNGGNATCFAYGQTGAGKTYTMIGTHEN
PGLYALAAKDIFRQLEVSQPRKHLFVWISFYEIYCGQLYDLLNRRKRLFAREDSKHMVQ
IVGLQELQVDSVELLLEVILKGSKERSTGATGVNADSSRSHAVIQIQIKDSAKRTFGRI
SFIDLAGSERAADARDSDRQTKMEGAEINQSLLALKECIRALDQEHTHTPFRQSKLTQV
LKDSFIGNAKTCMIANISPSHVATEHTLNTLRYADRVKELKKGIKCCTSVTSRNRTSGN
SLEHHHHHH*

FIG. 6

```
                        SEQUENCE LISTING

<160> NUMBER OF SEQ ID NOS: 10

<210> SEQ ID NO 1
<211> LENGTH: 6409
<212> TYPE: DNA
<213> ORGANISM: Artificial Sequence
<220> FEATURE:
<223> OTHER INFORMATION: Description of Artificial Sequence:KinI-3
      sequence

<400> SEQUENCE: 1
gcggccgcga attcggcacg aggctggccg ccgccggtgg ctcccgggtt gacgggactg      60
ttaggttgcg ggctttgggg ctcactcccg acggcattgt cttctcctct tctcagacag     120
ggcagaccga ggagtttgga ccgagagttt atagaaacct attcaccaaa atggcatcct     180
ggttatatga atgtctttgt gaagctgaac ttgcacagta ttattctcat ttcactgccc     240
ttggccttca gaaaatagat gaattagcca agattacaat gaaggactac tccaaattag     300
gagtccatga catgaacgac cgcaaacgtc tcttccaact tatcaaaatt attaagatta     360
tgcaagaaga agataaagca gtcagtatcc cagagcgtca tcttcagaca agcagcctgc     420
gcatcaaatc tcaggaatta agatctggcc ctcgcagaca gctgaatttt gattctcctg     480
ctgacaataa agacagaaat gccagcaatg atgggtttga aatgtgcagt ttatcagatt     540
tctctgcaaa tgaacagaag tccacttacc taaaagtgct agaacacatg ctaccagatg     600
attcccagta ccatacaaaa acaggaattc tgaatgccac agctggtgat tcctatgtgc     660
aaacagaaat cagcacttca ctcttttcac caaattacct ttctgcaata ctgggggatt     720
gtgatattcc cattattcaa agaatctctc atgtttcagg gtataactat ggaatccctc     780
attcttgtat cagacagaac acttcagaga aacagaatcc ttggactgag atggagaaaa     840
tcagagtttg tgttcgaaaa cgcccccttg gcatgaggga ggtacgtcgt ggagaaatta     900
atattattac tgtagaagac aaagaaactc tacttgtgca tgagaagaaa gaagcagttg     960
acctcactca atatattctg cagcatgttt tttattttga tgaagtcttt ggtgaggcgt    1020
gcaccaatca ggatgtatac atgaagacta ctcacccact tattcagcat attttcaatg    1080
gaggcaatgc cacttgcttt gcttatggac agacaggtgc tggaaagacc tacaccatga    1140
taggaactca tgagaaccca ggattgtatg ctctagctgc caaagatatc ttcaggcaac    1200
tagaagtgtc ccagccaaga aagcacctct ttgtgtggat cagcttctat gaaatttact    1260
gtggacagct ttatgacctc ctaaatagaa gaaaaaggct cttttgcaaga gaagatagca    1320 agcacatggt gcagatagtg ggactgcaag agcttcaggt ggacagtgtg gagctcctct    1380
tagaggtgat cttaaagggc agcaaggagc gcagcactgg ggccactgga gttaatgcag    1440
```

-continued

```
actcctcccg ctcccatgcc gtcatccaaa ttcagatcaa agattcagcc aagaggacat   1500
ttggcaggat ctcttttatt gacttggctg gcagtgaaag agcagcagat gcaagggact   1560
cagatagaca gacaaagatg gaaggtgcag aaataaatca gagtctactg gctctgaagg   1620
aatgtatccg agcactggat caggaacaca cccatactcc cttcaggcaa agcaaactaa   1680
ctcaggtcct gaaggactct ttcatcggca atgccaaaac ctgcatgatc gccaacatct   1740
caccaagcca cgtggccact gaacacactc tcaacacctt gcgctatgct gaccgggtca   1800
aagaactaaa gaaaggcatt aagtgttgca cttcagttac cagtcgaaat cggacatctg   1860
gaaactcctc tccaaaacga attcagagct cccctgtggc tttgtcagag acaaatgtt   1920
ctcccaaaaa agtcaagctg ggatttcagc agtcactcac agtggcagcc cctggttcca   1980
cgagagggaa ggtccatcct ctgaccagcc acccacccaa cattccttt acttctgcac   2040
ctaaggtctc tggtaaaagg ggtggctcca gagggagtcc ttcacaagag tgggtcattc   2100
atgctagccc tgtgaaagga actgtgcgct ctggacatgt ggccaaaaaa aagccagaag   2160
agtcagcacc attgtgctct gagaaaaatc gaatgggcaa caaaactgtc cttgggtggg   2220
aaagcagggc ctcaggccca ggagaaggcc tagtgcgtgg taagctgtcc accaagtgca   2280
agaaagtgca gacagtgcag ccagtacaga agcagcttgt gtctcgagtt gagctctcct   2340
ttggcaacgc ccaccacagg gctgagtaca gtcaagacga ccagagggc acgcctgcta   2400
ggcctgcctc tgaagcttgg acaaacatcc cgccacatca aaggagagg gaggaacatc   2460
tgcgtttcta tcaccagcag ttccaacagc cacctctcct ccaacagaag ttaaaatacc   2520
aaccactgaa aagtctttta cgccagtaca ggccccaga gggtcagctc acgaatgaga   2580
ctccgcctct gttccactct tactctgaaa accatgatgg agcccaagta gaggaacttg   2640
atgacagtga tttcagtgaa gattcttttt cacacatctc tagtcagagg gccacaaagc   2700
aaaggaacac cctggagaat agcgaagact cattcttcct gcaccagacg tggggacagg   2760
gtcctgagaa gcaggtggca gaaagacagc agagtctgtt ttctagcccc aggacaggtg   2820
acaagaaaga tctaactaaa agctgggtgg actccaggga cccataaac cacagaagag   2880
cagcactcga tcacagctgc agcccaagta aggggcccgt ggactggagc agagagaact   2940
ctacttcctc agggccttct cccagagaca gcctggcaga aagccatac tgttcacagg   3000
tagatttcat atatagacag gaaagaggtg gaggctcttc ctttgatctc agaaaggatg   3060
cctcccaaag tgaggtttct ggggagaatg agggcaactt gccatcccca gaggaagatg   3120
gtttcactat ctcattgtcc cacgttgcag ttcctggatc cccagaccaa agagacacag   3180
tcaccacacc tctgagagaa gtcagtgcag acggcccaat ccaggtgacc agcactgtga   3240
aaaacggtca tgctgtccca ggagaggatc ctagggggca gttaggcacg catgctgaat   3300
atgcttctgg actcatgtct ccctcacca tgtccctcct ggagaaccca gacaacgaag   3360
ggtctcctcc ctcggagcag ctggtccagg atggggctac gcacagtcta gtggcagaga   3420
gcacagggg cccagttgtg agccacacag tgccatctgg tgatcaagag gcagccttgc   3480
cagtgtcttc agcaactagg cacctgtggc tgtcctcatc tcccctgat aataagcctg   3540
gtggtgatct tccagctctg tccccatcac ccatccgtca gcacccagct gacaagctgc   3600
ccagcaggga ggcagaccta ggagaggcct gccagagcag agagactgta cttttctccc   3660
acgaacacat gggtagtgag cagtatgatg ctgatgcaga ggagacgggg ctggatggct   3720
cctgggggttt cccaggaaag ccccttcacca ccatacatat gggggtaccc cattctggac   3780
```

```
ctacactcac cccacgaaca ggaagtagtg atgtggctga ccagctctgg gcccaggaga   3840
gaaaacatcc tacaaggctt ggttggcagg agtttggttt gtccacagac cccatcaagt   3900
tgccctgcaa cagtgaaaat gtcacatggc tcaaacccag gccgatctca aggtgcttag   3960
caaggccaag ttctcccttg gttcccagct gctctcccaa gactgcaggg acactccgtc   4020
agcccaccct ggagcaagcg cagcaggtgg tcatccgagc acaccaggaa cagctggatg   4080 aaaatggctga gctcggcttc aaggaggaga cgctgatgag ccagctggct tctaatgatt   4140
ttgaagattt tgtgacccag ctggatgaaa tcatggttct gaaatccaag tgtatccaga   4200
gtctgaggag ccagctgcag ctctatctca cctgccacgg gccaccgca gcccctgagg    4260 gaacagtgcc gtcttagagc cagaccctgt gccgagatgg tgggggccct gcaggagtct   4320
gtgctgggct ctcaggctgg aggagcctct gccaggtcct ccctgcacac accagaaccc   4380
acacgctggt cctgcctatg ctagcgtcac cccagcccca cgtggcttca gataggtccc   4440
agcttctccc tcaggacag gcccctgtcc ctcagttcca tgcacaggag tgcctccaag    4500
ggtgggccag gccgaagaac ctaatgcctt tcccttgtgc ctagagaata tgattaacta   4560 acccctttgcc tgtgggaata tatttgggtc taataacccct gaagtttcta agtttgggga  4620
tcagaggatg gggtggtcag tggtagccta gaggtcagag gtcacaagac agagaagaca   4680
acatgctgag accagaggct tcaccagctg aattctgtgc ctaacttaga agactaaaca   4740
ctggcccaaa cttaaccatt ggtgctaggg ggacaggggt ggggtgagct ctgccccatc    4800
agcccttgga gattgatttg gggatttaga ggcgtttttg aaaatgtaaa tagcataaac   4860
cttgacttga tgtgtcactg acagcagcag atgtgagaca ggccttatat ttacagctcc   4920
cttcccttcc tgcaatccag tgttgaggca gaagagggtg cctgtgtcac acatcaattt   4980
ttctcctgac ttttgctcgg gtgaaaggcc tctgtacaat gcccgatact ctcatgcttc   5040
catggcagct cctggctcct atctgggaca cctcactacc cagcccccctc atggaatagt   5100 ccatctccta gcctggcctt catccagttc accctgccca gccaccctgc ctctcagggg   5160
tctgtgttgg gaaccttggc agttgaacag agtgctctgt tcaacagtct gaggcctctg   5220
aaacagaatt cacacacaaa ccttcagcca agttctgcct gctgtgtatc tttttagcag   5280
gaagcagctc aggacaggga agacaaagta gcctccaggt gccaattact ttaaagccac   5340
tctgggtcaa atggagattc atgagtcacg gccttggccc gaacgcccat tactatgtga   5400 gccttattt ccttcagata aaggataact ttttacggtt ttaaaaggag ggcttaatta    5460
aaaggccaag aagagggtta aatggctctc ttgagacact agcagcctgg tccagtcacc   5520
ctttgtcagc ctgacagtgc ctcatctgac cgccaggggg catccttatt ggtgcttccc   5580
ggctgcaggg cactgcggcc cctccctcac atgatcacta aaaaccttca aagacccagt   5640
ctagccaaaa gctcaagtgg gacaatggca cagtattaag gtcaaggaca aaaacttact   5700
tactttagga atgaaccta ttctatcatc atatacaaca gcaccactga gagctggtga    5760
aacagtttaa atcccatcct ctgcttgtgg caaatgatgc ataaatgcct gctgctcaca   5820
gtaaaagggc ttcttcctct tttactgggt gatcccctg aaggcccagc ctatcccaac    5880
tccacagtca ggaaggccta cgtccttggt ccacagacgg agctgggcca ggtttaaaag   5940
actcagtcta ggcttgcctt tgcaaaccaa aaacgaggac aggtctgaag tgggaagaaa   6000
gctccgaaat agaaaacggt taggtcctat tctatcccca gcaaatctaa gcaagaaatc   6060
tctttataca ccacatggcc cccccactcc cataaaacag ccttggtaat aaagaagtta   6120
tcacaccaag acataccttt tagattttta ttagtagttc tctctgaaga atcaaaatag   6180
```

-continued

```
ttagttagca aattatttta gattcaagac tgtatatcct ttgtatttag atctttaatg    6240
atgtacaaca taatacaaaa caaaccagag agactgattt ctaaaaaaaa aaaaaaaaa    6300 aaaaaaaaaa aaaaaaaaaa aaaaaaaaaa aaaaaaaaaa aaaaaaaaaa aaaaaaaaaa   6360
aaaaaaaaaa aaaaaaaaaa aaaaaaaaaa aaaaaaaaa aaaaaaaaa               6409
```

<210> SEQ ID NO 2
<211> LENGTH: 1368
<212> TYPE: PRT
<213> ORGANISM: Artificial Sequence
<220> FEATURE:
<223> OTHER INFORMATION: Description of Artificial Sequence: KinI-3 motor domain fragment

<400> SEQUENCE: 2

```
Met Ala Ser Trp Leu Tyr Glu Cys Leu Cys Glu Ala Glu Leu Ala Gln
 1               5                  10                  15

Tyr Tyr Ser His Phe Thr Ala Leu Gly Leu Gln Lys Ile Asp Glu Leu
            20                  25                  30

Ala Lys Ile Thr Met Lys Asp Tyr Ser Lys Leu Gly Val His Asp Met
        35                  40                  45

Asn Asp Arg Lys Arg Leu Phe Gln Leu Ile Lys Ile Ile Lys Ile Met
    50                  55                  60

Gln Glu Glu Asp Lys Ala Val Ser Ile Pro Glu Arg His Leu Gln Thr
65                  70                  75                  80

Ser Ser Leu Arg Ile Lys Ser Gln Glu Leu Arg Ser Gly Pro Arg Arg
                85                  90                  95

Gln Leu Asn Phe Asp Ser Pro Ala Asp Asn Lys Asp Arg Asn Ala Ser
            100                 105                 110

Asn Asp Gly Phe Glu Met Cys Ser Leu Ser Asp Phe Ser Ala Asn Glu
        115                 120                 125

Gln Lys Ser Thr Tyr Leu Lys Val Leu Glu His Met Leu Pro Asp Asp
    130                 135                 140

Ser Gln Tyr His Thr Lys Thr Gly Ile Leu Asn Ala Thr Ala Gly Asp
145                 150                 155                 160

Ser Tyr Val Gln Thr Glu Ile Ser Thr Ser Leu Phe Ser Pro Asn Tyr
                165                 170                 175

Leu Ser Ala Ile Leu Gly Asp Cys Asp Ile Pro Ile Ile Gln Arg Ile
            180                 185                 190

Ser His Val Ser Gly Tyr Asn Tyr Gly Ile Pro His Ser Cys Ile Arg
        195                 200                 205

Gln Asn Thr Ser Glu Lys Gln Asn Pro Trp Thr Glu Met Glu Lys Ile
    210                 215                 220

Arg Val Cys Val Arg Lys Arg Pro Leu Gly Met Arg Glu Val Arg Arg
225                 230                 235                 240

Gly Glu Ile Asn Ile Ile Thr Val Glu Asp Lys Glu Thr Leu Leu Val
                245                 250                 255

His Glu Lys Lys Glu Ala Val Asp Leu Thr Gln Tyr Ile Leu Gln His
            260                 265                 270

Val Phe Tyr Phe Asp Glu Val Phe Gly Glu Ala Cys Thr Asn Gln Asp
        275                 280                 285

Val Tyr Met Lys Thr Thr His Pro Leu Ile Gln His Ile Phe Asn Gly
    290                 295                 300

Gly Asn Ala Thr Cys Phe Ala Tyr Gly Gln Thr Gly Ala Gly Lys Thr
305                 310                 315                 320
```

-continued

```
Tyr Thr Met Ile Gly Thr His Glu Asn Pro Gly Leu Tyr Ala Leu Ala
            325                 330                 335

Ala Lys Asp Ile Phe Arg Gln Leu Glu Val Ser Gln Pro Arg Lys His
        340                 345                 350

Leu Phe Val Trp Ile Ser Phe Tyr Glu Ile Tyr Cys Gly Gln Leu Tyr
            355                 360                 365

Asp Leu Leu Asn Arg Arg Lys Arg Leu Phe Ala Arg Glu Asp Ser Lys
        370                 375                 380

His Met Val Gln Ile Val Gly Leu Gln Glu Leu Gln Val Asp Ser Val
385                 390                 395                 400

Glu Leu Leu Leu Glu Val Ile Leu Lys Gly Ser Lys Glu Arg Ser Thr
                405                 410                 415

Gly Ala Thr Gly Val Asn Ala Asp Ser Arg Ser His Ala Val Ile
            420                 425                 430

Gln Ile Gln Ile Lys Asp Ser Ala Lys Arg Thr Phe Gly Arg Ile Ser
        435                 440                 445

Phe Ile Asp Leu Ala Gly Ser Glu Arg Ala Ala Asp Ala Arg Asp Ser
    450                 455                 460

Asp Arg Gln Thr Lys Met Glu Gly Ala Glu Ile Asn Gln Ser Leu Leu
465                 470                 475                 480

Ala Leu Lys Glu Cys Ile Arg Ala Leu Asp Gln Glu His Thr His Thr
                485                 490                 495

Pro Phe Arg Gln Ser Lys Leu Thr Gln Val Leu Lys Asp Ser Phe Ile
            500                 505                 510

Gly Asn Ala Lys Thr Cys Met Ile Ala Asn Ile Ser Pro Ser His Val
        515                 520                 525

Ala Thr Glu His Thr Leu Asn Thr Leu Arg Tyr Ala Asp Arg Val Lys
    530                 535                 540

Glu Leu Lys Lys Gly Ile Lys Cys Cys Thr Ser Val Thr Ser Arg Asn
545                 550                 555                 560

Arg Thr Ser Gly Asn Ser Ser Pro Lys Arg Ile Gln Ser Ser Pro Gly
                565                 570                 575

Ala Leu Ser Glu Asp Lys Cys Ser Pro Lys Val Lys Leu Gly Phe
            580                 585                 590

Gln Gln Ser Leu Thr Val Ala Ala Pro Gly Ser Thr Arg Gly Lys Val
        595                 600                 605

His Pro Leu Thr Ser His Pro Pro Asn Ile Pro Phe Thr Ser Ala Pro
    610                 615                 620

Lys Val Ser Gly Lys Arg Gly Gly Ser Arg Gly Ser Pro Ser Gln Glu
625                 630                 635                 640

Trp Val Ile His Ala Ser Pro Val Lys Gly Thr Val Arg Ser Gly His
                645                 650                 655

Val Ala Lys Lys Lys Pro Glu Glu Ser Ala Pro Leu Cys Ser Glu Lys
            660                 665                 670

Asn Arg Met Gly Asn Lys Thr Val Leu Gly Trp Glu Ser Arg Ala Ser
        675                 680                 685

Gly Pro Gly Glu Gly Leu Val Arg Gly Lys Leu Ser Thr Lys Cys Lys
    690                 695                 700

Lys Val Gln Thr Val Gln Pro Val Gln Lys Gln Leu Val Ser Arg Val
705                 710                 715                 720

Glu Leu Ser Phe Gly Asn Ala His His Arg Ala Glu Tyr Ser Gln Asp
                725                 730                 735
```

-continued

```
Ser Gln Arg Gly Thr Pro Ala Arg Pro Ala Ser Glu Ala Trp Thr Asn
            740                 745                 750
Ile Pro Pro His Gln Lys Glu Arg Glu Glu His Leu Arg Phe Tyr His
        755                 760                 765
Gln Gln Phe Gln Gln Pro Leu Leu Gln Gln Lys Leu Lys Tyr Gln
770                 775                 780
Pro Leu Lys Arg Ser Leu Arg Gln Tyr Arg Pro Pro Glu Gly Gln Leu
785                 790                 795                 800
Thr Asn Glu Thr Pro Pro Leu Phe His Ser Tyr Ser Glu Asn His Asp
                805                 810                 815
Gly Ala Gln Val Glu Leu Asp Asp Ser Asp Phe Ser Glu Asp Ser
            820                 825                 830
Phe Ser His Ile Ser Ser Gln Arg Ala Thr Lys Gln Arg Asn Thr Leu
                835                 840                 845
Glu Asn Ser Glu Asp Ser Phe Phe Leu His Gln Thr Trp Gly Gln Gly
850                 855                 860
Pro Glu Lys Gln Val Ala Glu Arg Gln Gln Ser Leu Phe Ser Ser Pro
865                 870                 875                 880
Arg Thr Gly Asp Lys Lys Asp Leu Thr Lys Ser Trp Val Asp Ser Arg
                885                 890                 895
Asp Pro Ile Asn His Arg Ala Ala Leu Asp His Ser Cys Ser Pro
                900                 905                 910
Ser Lys Gly Pro Val Asp Trp Ser Arg Glu Asn Ser Thr Ser Ser Gly
        915                 920                 925
Pro Ser Pro Arg Asp Ser Leu Ala Glu Lys Pro Tyr Cys Ser Gln Val
        930                 935                 940
Asp Phe Ile Tyr Arg Gln Glu Arg Gly Gly Ser Ser Phe Asp Leu
945                 950                 955                 960
Arg Lys Asp Ala Ser Gln Ser Glu Val Ser Gly Glu Asn Gly Asn
                965                 970                 975
Leu Pro Ser Pro Glu Glu Asp Gly Phe Thr Ile Ser Leu Ser His Val
                980                 985                 990
Ala Val Pro Gly Ser Pro Asp Gln Arg Asp Thr Val Thr Thr Pro Leu
            995                 1000                1005
Arg Glu Val Ser Ala Asp Gly Pro Ile Gln Val Thr Ser Thr Val Lys
    1010                1015                1020
Asn Gly His Ala Val Pro Gly Glu Asp Pro Arg Gly Gln Leu Gly Thr
1025                1030                1035                1040
His Ala Glu Tyr Ala Ser Gly Leu Met Ser Pro Leu Thr Met Ser Leu
                1045                1050                1055
Leu Glu Asn Pro Asp Asn Glu Gly Ser Pro Ser Glu Gln Leu Val
            1060                1065                1070
Gln Asp Gly Ala Thr His Ser Leu Val Ala Glu Ser Thr Gly Gly Pro
    1075                1080                1085
Val Val Ser His Thr Val Pro Ser Gly Asp Gln Glu Ala Ala Leu Pro
    1090                1095                1100
Val Ser Ser Ala Thr Arg His Leu Trp Leu Ser Ser Pro Pro Asp
1105                1110                1115                1120
Asn Lys Pro Gly Gly Asp Leu Pro Ala Leu Ser Pro Ser Pro Ile Arg
            1125                1130                1135
Gln His Pro Ala Asp Lys Leu Pro Ser Arg Glu Ala Asp Leu Gly Glu
                1140                1145                1150
Ala Cys Gln Ser Arg Glu Thr Val Leu Phe Ser His Glu His Met Gly
```

-continued

```
      1155                1160                1165
Ser Glu Gln Tyr Asp Ala Asp Ala Glu Glu Thr Gly Leu Asp Gly Ser
    1170                1175                1180

Trp Gly Phe Pro Gly Lys Pro Phe Thr Thr Ile His Met Gly Val Pro
1185                1190                1195                1200

His Ser Gly Pro Thr Leu Thr Pro Arg Thr Gly Ser Ser Asp Val Ala
        1205                1210                1215

Asp Gln Leu Trp Ala Gln Glu Arg Lys His Pro Thr Arg Leu Gly Trp
    1220                1225                1230

Gln Glu Phe Gly Leu Ser Thr Asp Pro Ile Lys Leu Pro Cys Asn Ser
    1235                1240                1245

Glu Asn Val Thr Trp Leu Lys Pro Arg Pro Ile Ser Arg Cys Leu Ala
    1250                1255                1260

Arg Pro Ser Ser Pro Leu Val Pro Ser Cys Ser Pro Lys Thr Ala Gly
1265                1270                1275                1280

Thr Leu Arg Gln Pro Thr Leu Glu Gln Ala Gln Val Val Ile Arg
        1285                1290                1295

Ala His Gln Glu Gln Leu Asp Glu Met Ala Glu Leu Gly Phe Lys Glu
        1300                1305                1310

Glu Thr Leu Met Ser Gln Leu Ala Ser Asn Asp Phe Glu Asp Phe Val
        1315                1320                1325

Thr Gln Leu Asp Glu Ile Met Val Leu Lys Ser Lys Cys Ile Gln Ser
    1330                1335                1340

Leu Arg Ser Gln Leu Gln Leu Tyr Leu Thr Cys His Gly Pro Thr Ala
1345                1350                1355                1360

Ala Pro Glu Gly Thr Val Pro Ser
            1365
```

<210> SEQ ID NO 3
<211> LENGTH: 1122
<212> TYPE: DNA
<213> ORGANISM: Artificial Sequence
<220> FEATURE:
<223> OTHER INFORMATION: Description of Artificial Sequence: Fragment
      encoding residues D183-L546 with flanking vector sequence.

<400> SEQUENCE: 3

```
atggattgtg atattcccat tattcaaaga atctctcatg tttcagggta taactatgga      60
atccctcatt cttgtatcag acagaacact tcagagaaac agaatccttg gactgagatg     120
gagaaaatca gagtttgtgt tcgaaaacgc ccccctgggca tgagggaggt acgtcgtgga    180
gaaattaata ttattactgt agaagacaaa gaaactctac ttgtgcatga agaaagaa      240
gcagttgacc tcactcaata tattctgcag catgtttttt attttgatga agtctttggt     300
gaggcgtgca ccaatcagga tgtatacatg aagactactc acccacttat tcagcatatt     360
ttcaatggag gcaatgccac ttgctttgct tatggacaga caggtgctgg aaagacctac     420
accatgatag aactcatgaa gaacccagga ttgtatgctc tagctgccaa agatatcttc     480
aggcaactag aagtgtccca gccaagaaag caccctcttttg tgtggatcag cttctatgaa    540
atttactgtg acagctttta tgacctccta aatagaagaa aaaggctctt tgcaagagaa     600
gatagcaagc acatggtgca gatagtggga ctgcaagagc ttcaggtgga cagtgtggag    660
ctcctcttag aggtgatctt aaagggcagc aaggagcgca gcactggggc cactggagtt    720
aatgcagact cctcccgctc ccatgccgtc atccaaattc agatcaaaga ttcagccaag    780
aggacatttg gcaggatctc tttttattgac ttggctggca gtgaaagagc agcagatgca    840
```

-continued

```
agggactcag atagacagac aaagatggaa ggtgcagaaa taaatcagag tctactggct   900
ctgaaggaat gtatccgagc actggatcag gaacacaccc atactccctt caggcaaagc   960
aaactaactc aggtcctgaa ggactctttc atcggcaatg ccaaaacctg catgatcgcc  1020
aacatctcac caagccacgt ggccactgaa cacactctca acaccttgcg ctatgctgac  1080
cgggtcaaag aactactcga gcaccaccac caccaccact ga                     1122
```

<210> SEQ ID NO 4
<211> LENGTH: 373
<212> TYPE: PRT
<213> ORGANISM: Artificial Sequence
<220> FEATURE:
<223> OTHER INFORMATION: Description of Artificial Sequence: Fragment encoding residues D183-L546 with flanking vector sequence.

<400> SEQUENCE: 4

```
Met Asp Cys Asp Ile Pro Ile Ile Gln Arg Ile Ser His Val Ser Gly
  1               5                  10                  15

Tyr Asn Tyr Gly Ile Pro His Ser Cys Ile Arg Gln Asn Thr Ser Glu
             20                  25                  30

Lys Gln Asn Pro Trp Thr Glu Met Glu Lys Ile Arg Val Cys Val Arg
         35                  40                  45

Lys Arg Pro Leu Gly Met Arg Glu Val Arg Arg Gly Glu Ile Asn Ile
     50                  55                  60

Ile Thr Val Glu Asp Lys Glu Thr Leu Leu Val His Glu Lys Lys Glu
 65                  70                  75                  80

Ala Val Asp Leu Thr Gln Tyr Ile Leu Gln His Val Phe Tyr Phe Asp
                 85                  90                  95

Glu Val Phe Gly Glu Ala Cys Thr Asn Gln Asp Val Tyr Met Lys Thr
            100                 105                 110

Thr His Pro Leu Ile Gln His Ile Phe Asn Gly Gly Asn Ala Thr Cys
        115                 120                 125

Phe Ala Tyr Gly Gln Thr Gly Ala Gly Lys Thr Tyr Thr Met Ile Gly
    130                 135                 140

Thr His Glu Asn Pro Gly Leu Tyr Ala Leu Ala Ala Lys Asp Ile Phe
145                 150                 155                 160

Arg Gln Leu Glu Val Ser Gln Pro Arg Lys His Leu Phe Val Trp Ile
                165                 170                 175

Ser Phe Tyr Glu Ile Tyr Cys Gly Gln Leu Tyr Asp Leu Leu Asn Arg
            180                 185                 190

Arg Lys Arg Leu Phe Ala Arg Glu Asp Ser Lys His Met Val Gln Ile
        195                 200                 205

Val Gly Leu Gln Glu Leu Gln Val Asp Ser Val Glu Leu Leu Leu Glu
    210                 215                 220

Val Ile Leu Lys Gly Ser Lys Glu Arg Ser Thr Gly Ala Thr Gly Val
225                 230                 235                 240

Asn Ala Asp Ser Ser Arg Ser His Ala Val Ile Gln Ile Gln Ile Lys
                245                 250                 255

Asp Ser Ala Lys Arg Thr Phe Gly Arg Ile Ser Phe Ile Asp Leu Ala
            260                 265                 270

Gly Ser Glu Arg Ala Ala Asp Ala Arg Asp Ser Asp Arg Gln Thr Lys
        275                 280                 285

Met Glu Gly Ala Glu Ile Asn Gln Ser Leu Leu Ala Leu Lys Glu Cys
    290                 295                 300
```

```
Ile Arg Ala Leu Asp Gln Glu His Thr His Thr Pro Phe Arg Gln Ser
305                 310                 315                 320

Lys Leu Thr Gln Val Leu Lys Asp Ser Phe Ile Gly Asn Ala Lys Thr
            325                 330                 335

Cys Met Ile Ala Asn Ile Ser Pro Ser His Val Ala Thr Glu His Thr
        340                 345                 350

Leu Asn Thr Leu Arg Tyr Ala Asp Arg Val Lys Glu Leu Leu Glu His
    355                 360                 365

His His His His His
        370

<210> SEQ ID NO 5
<211> LENGTH: 1146
<212> TYPE: DNA
<213> ORGANISM: Artificial Sequence
<220> FEATURE:
<223> OTHER INFORMATION: Description of Artificial Sequence: Fragment
      encoding residues V195 - S566 with flanking vector sequence.

<400> SEQUENCE: 5
atggtttcag ggtataacta tggaatccct cattcttgta tcagacagaa cacttcagag      60
aaacagaatc cttggactga gatggagaaa tcagagtttt gtgttcgaaa acgccccctg    120
ggcatgaggg aggtacgtcg tggagaaatt aatattatta ctgtagaaga caaagaaact    180
ctacttgtgc atgagaagaa agaagcagtt gacctcactc aatatattct gcagcatgtt    240
tttatttttg atgaagtctt tggtgaggcg tgcaccaatc aggatgtata catgaagact    300
actcacccac ttattcagca tattttcaat ggaggcaatg ccacttgctt tgcttatgga    360
cagacaggtg ctggaaagac ctacaccatg ataggaactc atgagaaccc aggattgtat    420
gctctagctg ccaaagatat cttcaggcaa ctagaagtgt cccagccaag aaagcacctc    480
tttgtgtgga tcagcttcta tgaaatttac tgtggacagc tttatgacct cctaaataga    540 agaaaaggc tctttgcaag agaagatagc aagcacatgt gcagatagt gggactgcaa    600 gagcttcagg tggacagtgt ggagctcctc ttagaggtga tcttaaaggg cagcaaggag    660
cgcagcactg gggccactgg agttaatgca gactcctccc gctcccatgc cgtcatccaa    720
attcagatca aagattcagc caagaggaca tttggcagga tctcttttat tgacttggct    780
ggcagtgaaa gagcagcaga tgcaagggac tcagatagac agacaaagat ggaaggtgca    840 gaaataaaatc agagtctact ggctctgaag aatgtatcc gagcactgga tcaggaacac    900
acccatactc ccttcaggca aagcaaacta actcaggtcc tgaaggactc tttcatcggc    960
aatgccaaaa cctgcatgat cgccaacatc tcaccaagcc acgtggccac tgaacacact   1020
ctcaacacct tgcgctatgc tgaccgggtc aaagaactaa agaaaggcat taagtgttgc   1080
acttcagtta ccagtcgaaa tcggacatct ggaaactccc tcgagcacca ccaccaccac   1140
cactga                                                              1146

<210> SEQ ID NO 6
<211> LENGTH: 381
<212> TYPE: PRT
<213> ORGANISM: Artificial Sequence
<220> FEATURE:
<223> OTHER INFORMATION: Description of Artificial Sequence: Peptide
      fragment V195-S566 with flanking vector sequence.

<400> SEQUENCE: 6

Met Val Ser Gly Tyr Asn Tyr Gly Ile Pro His Ser Cys Ile Arg Gln
1               5                   10                  15
```

```
Asn Thr Ser Glu Lys Gln Asn Pro Trp Thr Glu Met Glu Lys Ile Arg
             20                  25                  30

Val Cys Val Arg Lys Arg Pro Leu Gly Met Arg Glu Val Arg Arg Gly
         35                  40                  45

Glu Ile Asn Ile Ile Thr Val Glu Asp Lys Glu Thr Leu Leu Val His
     50                  55                  60

Glu Lys Lys Glu Ala Val Asp Leu Thr Gln Tyr Ile Leu Gln His Val
 65                  70                  75                  80

Phe Tyr Phe Asp Glu Val Phe Gly Glu Ala Cys Thr Asn Gln Asp Val
                 85                  90                  95

Tyr Met Lys Thr Thr His Pro Leu Ile Gln His Ile Phe Asn Gly Gly
             100                 105                 110

Asn Ala Thr Cys Phe Ala Tyr Gly Gln Thr Gly Ala Gly Lys Thr Tyr
         115                 120                 125

Thr Met Ile Gly Thr His Glu Asn Pro Gly Leu Tyr Ala Leu Ala Ala
     130                 135                 140

Lys Asp Ile Phe Arg Gln Leu Glu Val Ser Gln Pro Arg Lys His Leu
145                 150                 155                 160

Phe Val Trp Ile Ser Phe Tyr Glu Ile Tyr Cys Gly Gln Leu Tyr Asp
                 165                 170                 175

Leu Leu Asn Arg Arg Lys Arg Leu Phe Ala Arg Glu Asp Ser Lys His
             180                 185                 190

Met Val Gln Ile Val Gly Leu Gln Glu Leu Gln Val Asp Ser Val Glu
         195                 200                 205

Leu Leu Leu Glu Val Ile Leu Lys Gly Ser Lys Glu Arg Ser Thr Gly
     210                 215                 220

Ala Thr Gly Val Asn Ala Asp Ser Ser Arg Ser His Ala Val Ile Gln
225                 230                 235                 240

Ile Gln Ile Lys Asp Ser Ala Lys Arg Thr Phe Gly Arg Ile Ser Phe
                 245                 250                 255

Ile Asp Leu Ala Gly Ser Glu Arg Ala Ala Asp Ala Arg Asp Ser Asp
             260                 265                 270

Arg Gln Thr Lys Met Glu Gly Ala Glu Ile Asn Gln Ser Leu Leu Ala
         275                 280                 285

Leu Lys Glu Cys Ile Arg Ala Leu Asp Gln Glu His Thr His Thr Pro
     290                 295                 300

Phe Arg Gln Ser Lys Leu Thr Gln Val Leu Lys Asp Ser Phe Ile Gly
305                 310                 315                 320

Asn Ala Lys Thr Cys Met Ile Ala Asn Ile Ser Pro Ser His Val Ala
                 325                 330                 335

Thr Glu His Thr Leu Asn Thr Leu Arg Tyr Ala Asp Arg Val Lys Glu
             340                 345                 350

Leu Lys Lys Gly Ile Lys Cys Cys Thr Ser Val Thr Ser Arg Asn Arg
         355                 360                 365

Thr Ser Gly Asn Ser Leu Glu His His His His His His
370                 375                 380
```

<210> SEQ ID NO 7
<211> LENGTH: 1032
<212> TYPE: DNA
<213> ORGANISM: Artificial Sequence
<220> FEATURE:
<223> OTHER INFORMATION: Description of Artificial Sequence: Fragment
      encoding peptide E213 - L546.

-continued

```
<400> SEQUENCE: 7
atggagaaac agaatccttg gactgagatg gagaaaatca gagtttgtgt tcgaaaacgc      60 ccccctgggca tgagggaggt acgtcgtgga gaaattaata ttattactgt agaagacaaa    120
gaaactctac ttgtgcatga aagaaagaa gcagttgacc tcactcaata tattctgcag     180
catgtttttt attttgatga agtctttggt gaggcgtgca ccaatcagga tgtatacatg    240
aagactactc acccacttat tcagcatatt ttcaatggag caatgccac ttgctttgct     300 tatggacaga caggtgctgg aaagacctac accatgatag aactcatga aacccagga     360 ttgtatgctc tagctgccaa agatatcttc aggcaactga agtgtccca gccaagaaag    420 cacctctttg tgtggatcag cttctatgaa atttactgtg gacagcttta tgacctccta    480
aatagaagaa aaaggctctt tgcaagagaa gatagcaagc acatggtgca gatagtggga   540
ctgcaagagc ttcaggtgga cagtgtggag ctcctcttag aggtgatctt aaagggcagc   600
aaggagcgca gcactgggc cactggagtt aatgcagact cctcccgctc ccatgccgtc    660
atccaaattc agatcaaaga ttcagccaag aggacatttg gcaggatctc ttttattgac   720
ttggctggca gtgaaagagc agcagatgca agggactcag atagacagac aaagatggaa   780
ggtgcagaaa taaatcagag tctactggct ctgaaggaat gtatccgagc actggatcag   840
gaacacaccc atactccctt caggcaaagc aaactaactc aggtcctgaa ggactctttc   900
atcggcaatg ccaaaacctg catgatcgcc aacatctcac caagccacgt ggccactgaa    960
cacactctca acaccttgcg ctatgctgac cgggtcaaag aactactcga gcaccaccac  1020
caccaccact ga                                                        1032

<210> SEQ ID NO 8
<211> LENGTH: 343
<212> TYPE: PRT
<213> ORGANISM: Artificial Sequence
<220> FEATURE:
<223> OTHER INFORMATION: Description of Artificial Sequence: Peptide
      fragment E213-S546.

<400> SEQUENCE: 8

Met Glu Lys Gln Asn Pro Trp Thr Glu Met Glu Lys Ile Arg Val Cys
  1               5                  10                  15

Val Arg Lys Arg Pro Leu Gly Met Arg Glu Val Arg Arg Gly Glu Ile
                 20                  25                  30

Asn Ile Ile Thr Val Glu Asp Lys Glu Thr Leu Leu Val His Glu Lys
             35                  40                  45

Lys Glu Ala Val Asp Leu Thr Gln Tyr Ile Leu Gln His Val Phe Tyr
         50                  55                  60

Phe Asp Glu Val Phe Gly Glu Ala Cys Thr Asn Gln Asp Val Tyr Met
 65                  70                  75                  80

Lys Thr Thr His Pro Leu Ile Gln His Ile Phe Asn Gly Gly Asn Ala
                 85                  90                  95

Thr Cys Phe Ala Tyr Gly Gln Thr Gly Ala Gly Lys Thr Tyr Thr Met
            100                 105                 110

Ile Gly Thr His Glu Asn Pro Gly Leu Tyr Ala Leu Ala Ala Lys Asp
        115                 120                 125

Ile Phe Arg Gln Leu Glu Val Ser Gln Pro Arg Lys His Leu Phe Val
    130                 135                 140

Trp Ile Ser Phe Tyr Glu Ile Tyr Cys Gly Gln Leu Tyr Asp Leu Leu
145                 150                 155                 160
```

-continued

```
Asn Arg Arg Lys Arg Leu Phe Ala Arg Glu Asp Ser Lys His Met Val
            165                 170                 175
Gln Ile Val Gly Leu Gln Glu Leu Gln Val Asp Ser Val Glu Leu Leu
        180                 185                 190
Leu Glu Val Ile Leu Lys Gly Ser Lys Glu Arg Ser Thr Gly Ala Thr
        195                 200                 205
Gly Val Asn Ala Asp Ser Ser Arg Ser His Ala Val Ile Gln Ile Gln
    210                 215                 220
Ile Lys Asp Ser Ala Lys Arg Thr Phe Gly Arg Ile Ser Phe Ile Asp
225                 230                 235                 240
Leu Ala Gly Ser Glu Arg Ala Ala Asp Ala Arg Asp Ser Asp Arg Gln
                245                 250                 255
Thr Lys Met Glu Gly Ala Glu Ile Asn Gln Ser Leu Leu Ala Leu Lys
            260                 265                 270
Glu Cys Ile Arg Ala Leu Asp Gln Glu His Thr His Thr Pro Phe Arg
        275                 280                 285
Gln Ser Lys Leu Thr Gln Val Leu Lys Asp Ser Phe Ile Gly Asn Ala
    290                 295                 300
Lys Thr Cys Met Ile Ala Asn Ile Ser Pro Ser His Val Ala Thr Glu
305                 310                 315                 320
His Thr Leu Asn Thr Leu Arg Tyr Ala Asp Arg Val Lys Glu Leu Leu
                325                 330                 335
Glu His His His His His His
            340
```

<210> SEQ ID NO 9
<211> LENGTH: 1092
<212> TYPE: DNA
<213> ORGANISM: Artificial Sequence
<220> FEATURE:
<223> OTHER INFORMATION: Description of Artificial Sequence: Fragment encoding peptide E213 - S566.

<400> SEQUENCE: 9

```
atggagaaac agaatccttg gactgagatg gagaaaatca gagtttgtgt tcgaaaacgc      60
cccctgggca tgagggaggt acgtcgtgga gaaattaata ttattactgt agaagacaaa     120
gaaactctac ttgtgcatga agagaaagaa gcagttgacc tcactcaata tattctgcag     180
catgtttttt attttgatga agtctttggt gaggcgtgca ccaatcagga tgtatacatg     240
aagactactc acccacttat tcagcatatt tcaatggag gcaatgccac ttgctttgct     300
tatggacaga caggtgctgg aaagacctac accatgatag aactcatga acccagga      360
ttgtatgctc tagctgccaa agatatcttc aggcaactag aagtgtccca gccaagaaag     420
cacctctttg tgtggatcag cttctatgaa atttactgtg acagcttta tgacctccta     480
aatagaagaa aaaggctctt tgcaagagaa gatagcaagc acatggtgca gatagtggga     540
ctgcaagagc ttcaggtgga cagtgtggag ctcctcttag aggtgatctt aaagggcagc     600
aaggagcgca gcactgggc cactggagtt aatgcagact cctcccgctc ccatgccgtc     660
atccaaattc agatcaaaga ttcagccaag aggacatttg gcaggatctc ttttattgac     720
ttggctggca gtgaaagagc agcagatgca agggactcag atagacagac aaagatggaa     780
ggtgcagaaa taaatcagag tctactggct ctgaaggaat gtatccgagc actggatcag     840
gaacacaccc atactccctt caggcaaagc aaactaactc aggtcctgaa ggactctttc     900
atcggcaatg ccaaaacctg catgatcgcc aacatctcac caagccacgt ggccactgaa     960
```

-continued cacactctca acaccttgcg ctatgctgac cgggtcaaag aactaaagaa aggcattaag    1020
tgttgcactt cagttaccag tcgaaatcgg acatctggaa actccctcga gcaccaccac    1080
caccaccact ga                                                        1092

<210> SEQ ID NO 10
<211> LENGTH: 363
<212> TYPE: PRT
<213> ORGANISM: Artificial Sequence
<220> FEATURE:
<223> OTHER INFORMATION: Description of Artificial Sequence: Peptide
      fragment E213 - S566.

<400> SEQUENCE: 10

Met Glu Lys Gln Asn Pro Trp Thr Glu Met Glu Lys Ile Arg Val Cys
 1               5                  10                  15

Val Arg Lys Arg Pro Leu Gly Met Arg Glu Val Arg Arg Gly Glu Ile
                20                  25                  30

Asn Ile Ile Thr Val Glu Asp Lys Glu Thr Leu Leu Val His Glu Lys
            35                  40                  45

Lys Glu Ala Val Asp Leu Thr Gln Tyr Ile Leu Gln His Val Phe Tyr
        50                  55                  60

Phe Asp Glu Val Phe Gly Glu Ala Cys Thr Asn Gln Asp Val Tyr Met
 65                  70                  75                  80

Lys Thr Thr His Pro Leu Ile Gln His Ile Phe Asn Gly Gly Asn Ala
                85                  90                  95

Thr Cys Phe Ala Tyr Gly Gln Thr Gly Ala Gly Lys Thr Tyr Thr Met
               100                 105                 110

Ile Gly Thr His Glu Asn Pro Gly Leu Tyr Ala Leu Ala Ala Lys Asp
           115                 120                 125

Ile Phe Arg Gln Leu Glu Val Ser Gln Pro Arg Lys His Leu Phe Val
       130                 135                 140

Trp Ile Ser Phe Tyr Glu Ile Tyr Cys Gly Gln Leu Tyr Asp Leu Leu
145                 150                 155                 160

Asn Arg Arg Lys Arg Leu Phe Ala Arg Glu Asp Ser Lys His Met Val
               165                 170                 175

Gln Ile Val Gly Leu Gln Glu Leu Gln Val Asp Ser Val Glu Leu Leu
           180                 185                 190

Leu Glu Val Ile Leu Lys Gly Ser Lys Glu Arg Ser Thr Gly Ala Thr
       195                 200                 205

Gly Val Asn Ala Asp Ser Arg Ser His Ala Val Ile Gln Ile Gln
   210                 215                 220

Ile Lys Asp Ser Ala Lys Arg Thr Phe Gly Arg Ile Ser Phe Ile Asp
225                 230                 235                 240

Leu Ala Gly Ser Glu Arg Ala Ala Asp Ala Arg Asp Ser Asp Arg Gln
               245                 250                 255

Thr Lys Met Glu Gly Ala Glu Ile Asn Gln Ser Leu Leu Ala Leu Lys
           260                 265                 270

Glu Cys Ile Arg Ala Leu Asp Gln Glu His Thr His Thr Pro Phe Arg
       275                 280                 285

Gln Ser Lys Leu Thr Gln Val Leu Lys Asp Ser Phe Ile Gly Asn Ala
   290                 295                 300

Lys Thr Cys Met Ile Ala Asn Ile Ser Pro Ser His Val Ala Thr Glu
305                 310                 315                 320

His Thr Leu Asn Thr Leu Arg Tyr Ala Asp Arg Val Lys Glu Leu Lys
               325                 330                 335

-continued

```
Lys Gly Ile Lys Cys Cys Thr Ser Val Thr Ser Arg Asn Arg Thr Ser
            340                 345                 350

Gly Asn Ser Leu Glu His His His His His His
            355             360
```

KINI-3 MOTOR PROTEIN AND METHODS FOR ITS USE

CROSS-REFERENCE TO RELATED APPLICATION

The present application is a division of 09/967,908 filed Sep. 28, 2001, now U. S. Pat. No. 6,514,738 continuation-in-part of U.S. Ser. No. 09/675,227, filed Sep. 29, 2000, now U.S. Pat. No. 6,461,855, which is incorporated by reference in its entirety for all purposes.

FIELD OF THE INVENTION

The invention provides isolated nucleic acid and amino acid sequences of KinI-3 (Accession number AL353662), methods of detecting KinI-3 and screening for KinI-3 modulators using biologically active KinI-3, and kits for screening for KinI-3 modulators.

BACKGROUND OF THE INVENTION

The kinesin superfamily is an extended family of related microtubule motor proteins. It can be classified into at least 8 subfamilies based on primary amino acid sequence, domain structure, velocity of movement, and cellular function. This family is exemplified by "true" kinesin, which was first isolated from the axoplasm of squid, where it is believed to play a role in anterograde axonal transport of vesicles and organelles (see, e.g., Goldstein, *Annu. Rev. Genet.* 27:319–351 (1993)). Kinesin uses ATP to generate force and directional movement associated with microtubules.

Within this functional group of kinesins resides a group of kinesins from several organisms that share significant sequence homology, the Kin I subfamily, and that function to destabilize microtubule ends. These include *H. sapiens* MCAK (also known as mitotic centromere-associated kinesin or HsMCAK), *X. laevis* MCAK, and *C. griseus* MCAK.

Defects in function of these proteins would be expected to result in cell cycle arrest in mitosis. As such, compounds that modulate the activity of these kinesins may affect cellular proliferation. The present invention provides a novel method to identify such compounds.

The discovery of a new kinesin motor protein, and more particularly, one having sequence homology to MCAK, and the polynucleotides encoding it satisfies a need in the art by providing new compositions which are useful in the diagnosis, prevention, and treatment of cancer, neurological disorders, and disorders of vesicular transport.

SUMMARY OF THE INVENTION

The present invention is based on the discovery of a new human kinesin motor protein, KinI-3, the polynucleotide encoding KinI-3, and the use of these compositions for the diagnosis, treatment, or prevention of cancer, neurological disorders, and disorders of vesicular transport.

In one aspect, the invention provides an isolated nucleic acid sequence encoding a kinesin superfamily motor protein, wherein the motor protein has the following properties: (i) the protein's activity includes microtubule depolymerization activity; and (ii) the protein has a sequence that has greater than 70% amino acid sequence identity to SEQ ID NO:2 as measured using a sequence comparison algorithm. In one embodiment, the protein further specifically binds to polyclonal antibodies raised against SEQ ID NO:2.

In one embodiment, the nucleic acid encodes KinI-3 or a fragment thereof. In another embodiment, the nucleic acid encodes SEQ ID NO:2. In another embodiment, the nucleic acid has a nucleotide sequence of SEQ ID NO:1.

In one aspect, the nucleic acid comprises a sequence which encodes an amino acid sequence which has greater than 70% sequence identity with SEQ ID NO:2, or the motor domain thereof, preferably greater than 80%, more preferably greater than 90%, more preferably greater than 95% or, in another embodiment, has 98 to 100% sequence identity with SEQ ID NO:2.

In one embodiment, the nucleic acid comprises a sequence which has greater than 55 or 60% sequence identity with SEQ ID NO:1, or the segment encoding the motor domain thereof, preferably greater than 70%, more preferably greater than 80%, more preferably greater than 90 or 95% or, in another embodiment, has 98 to 100% sequence identity with SEQ ID NO:1. In another embodiment provided herein, the nucleic acid hybridizes under stringent conditions to a nucleic acid having a sequence or complementary sequence of SEQ ID NO:1.

In another aspect, the invention provides an expression vector comprising a nucleic acid encoding a kinesin superfamily motor protein, wherein the motor protein has the following properties: (i) the protein's activity includes microtubule depolymerization activity; and (ii) the protein has a sequence that has greater than 70% amino acid sequence identity to SEQ ID NO:2 as measured using a sequence comparison algorithm. The invention further provides a host cell transfected with the vector.

In another aspect, the invention provides an isolated kinesin superfamily motor protein, wherein the protein has one or more of the properties described above. In one embodiment, the protein specifically binds to polyclonal antibodies generated against a motor domain, tail domain or other fragment of KinI-3. In another embodiment, the protein comprises an amino acid sequence of SEQ ID NO:2.

In one aspect, the protein provided herein comprises an amino acid sequence which has greater than 70% sequence identity with SEQ ID NO:2, or the motor domain thereof, preferably greater than 80%, more preferably greater than 90%, more preferably greater than 95% or, in another embodiment, has 98 to 100% sequence identity with SEQ ID NO:2. The invention features a substantially purified polypeptide comprising the amino acid sequence of SEQ ID NO:2 or a fragment thereof and more particularly, the motor domain of the amino acid sequence of SEQ ID NO:2 or a fragment thereof.

In one embodiment, the present invention provides a method of identifying a candidate agent as a modulator of the activity of a target protein. The method comprises adding a candidate agent to a mixture comprising a target protein which directly or indirectly produces ADP or phosphate, under conditions that normally allow the production of ADP or phosphate. The method further comprises subjecting the mixture to a reaction that uses said ADP or phosphate as a substrate under conditions that normally allow the ADP or phosphate to be utilized and determining the level of activity of the reaction as a measure of the concentration of ADP or phosphate. A change in the level between the presence and absence of the candidate agent indicates a modulator of the target protein.

The phrase "use ADP or phosphate" means that the ADP or phosphate are directly acted upon by detection reagents. In one case, the ADP, for example, can be hydrolyzed or can be phosphorylated. As another example, the phosphate can be added to another compound. As used herein, in each of these cases, ADP or phosphate is acting as a substrate.

Preferably, the target protein either directly or indirectly produces ADP or phosphate and comprises a motor domain. More preferably, the target protein comprises a kinesin superfamily motor protein as described above and most preferably, the target protein comprises KinI-3 or a fragment thereof.

Also provided are modulators of the target protein including agents for the treatment of cellular proliferation, including cancer, hyperplasias, restenosis, cardiac hypertrophy, immune disorders and inflammation. The agents and compositions provided herein can be used in variety of applications which include the formulation of sprays, powders, and other compositions. Also provided herein are methods of treating cellular proliferation disorders such as cancer, hyperplasias, restenosis, cardiac hypertrophy, immune disorders and inflammation, for treating disorders associated with KinI-3 activity, and for inhibiting KinI-3.

BRIEF DESCRIPTION OF THE DRAWINGS

FIGS. 1A, B and C shows an embodiment of a nucleic acid sequence encoding a KinI-3 (SEQ ID NO:1). The motor domain is shown in bold.

FIG. 2 shows the amino acid sequence of a particularly preferred fragment of the motor domain of KinI-3 (SEQ ID NO:2).

FIG. 3 shows a nucleic acid (SEQ ID NO:3) and amino acid sequences (SEQ ID NO:4) of a fragment of containing residues D183 L546. Flanking residues from the pET23d vector are shown in bold.

FIG. 4 shows nucleic acid (SEQ. ID. NO:5) and amino acid sequences (SEQ ID NO:6) of a fragment of KinI-3 from V195 TO S566. Flanking vector sequences are shown in bold.

FIG. 5 shows nucleic acid (SEQ. ID. NO:7) and amino acid sequences (SEQ ID NO:8) of a fragment of KinI-3 from E213 to L546.

FIG. 6: shows nucleic acid (SEQ ID NO:9) and amino acid (SEQ ID NO:10) of a fragment of KinI-3 from E213 to S566.

DETAILED DESCRIPTION OF THE INVENTION

I. Definitions

Figure 7:
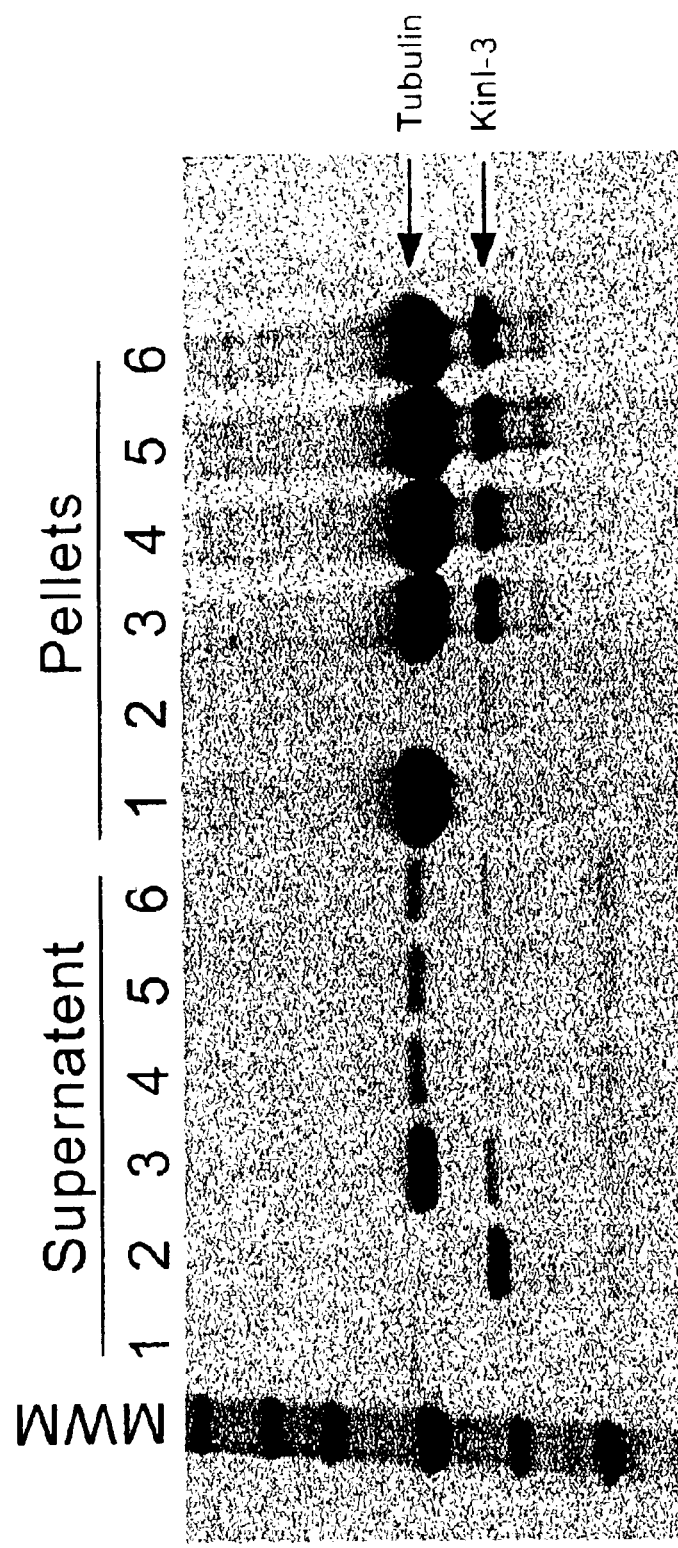
FIG. 7 shows ATP-dependent microtubule depolymerization activity of KinI-3 detected by presence of a tubulin band in the supernatant.

"ADP" refers to adenosine diphosphate and also includes ADP analogs, including, but not limited to, deoxyadenosine diphosphate (dADP) and adenosine analogs. "Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The term antibody also includes antibody fragments either produced by the modification of whole antibodies or those synthesized de novo using recombinant DNA methodologies.

An "anti-KinI-3" antibody is an antibody or antibody fragment that specifically binds a polypeptide encoded by the KinI-3 gene, cDNA, or a subsequence thereof.

"Biologically active" target protein refers to a target protein that has one or more of kinesin protein's biological activities, including, but not limited to microtubule depolymerization or polymerization activity, as tested, as described in the Examples. Biological activity can also be demonstrated in a microtubule gliding assay or a microtubule binding assay. Other possible activities include ATPase activity referring to ability to hydrolyze ATP., binding to other proteins of the spindle, binding to proteins involved in cell-cycle control, or serving as a substrate to other enzymes, such as kinases or proteases and specific kinesin cellular activities, such as chromosome congregation, axonal transport, etc.

"Biological sample" as used herein is a sample of biological tissue or fluid that contains a target protein or a fragment thereof or nucleic acid encoding a target protein or a fragment thereof. Biological samples may also include sections of tissues such as frozen sections taken for histologic purposes. A biological sample comprises at least one cell, preferably plant or vertebrate. Embodiments include cells obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

A "comparison window' includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the global alignment algorithm of Needleman & Wunsch, J. Mol. Biol. 48:443 (1970), by the search for similarity methods of Pearson & Lipman, Proc. Natl. Acad. Sci. USA 85:2444 (1988) and Altschul et al. Nucleic Acids Res. 25(17): 3389–3402 (1997), by computerized implementations of these algorithms (GAP, BESTFIT, FASTA, and BLAST in the Wisconsin Genetics Software Package, Genetics Computer Group, 575 Science Dr., Madison, Wis.), or by manual alignment and visual inspection (see, e.g., Ausubel et al., supra).

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another example of a useful algorithm implementation is PILEUP. PILEUP creates a multiple sequence alignment from a group of related sequences using progressive, pairwise alignments. It can also plot a dendrogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). As a general rule, PileUp can align up to 500 sequences, with any single sequence in the final alignment restricted to a maximum length of 7,000 characters.

The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment.

"Variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCT all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each degenerate codon in a nucleic acid can be modified to yield a functionally identical molecule. Accordingly, each silent variation of a nucleic acid which encodes a polypeptide is implicit in each described sequence.

Also included within the definition of target proteins of the present invention are amino acid sequence variants of wild-type target proteins. These variants fall into one or more of three classes: substitutional, insertional or deletional variants. These variants ordinarily are prepared by site specific mutagenesis of nucleotides in the DNA encoding the target protein, using cassette or PCR mutagenesis or other techniques well known in the art, to produce DNA encoding the variant, and thereafter expressing the DNA in recombinant cell culture. Variant target protein fragments having up to about 100–150 amino acid residues may be prepared by in vitro synthesis using established techniques. Amino acid sequence variants are characterized by the predetermined nature of the variation, a feature that sets them apart from naturally occurring allelic or interspecies variation of the target protein amino acid sequence. The variants typically exhibit the same qualitative biological activity as the naturally occurring analogue, although variants can also be selected which have modified characteristics.

Amino acid substitutions are typically of single residues; insertions usually will be on the order of from about 1 to about 20 amino acids, although considerably longer insertions may be tolerated. Deletions range from about 1 to about 20 residues, although in some cases, deletions may be much longer.

Substitutions, deletions, and insertions or any combinations thereof may be used to arrive at a final derivative. Generally, these changes are done on a few amino acids to minimize the alteration of the molecule. However, larger characteristics may be tolerated in certain circumstances.

Individual substitutions, to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (Henikoff and Henikoff (Proc. Natl. Acad. Sci. USA 89; 10915–10919 (1992))).

"Cytoskeletal component" denotes any molecule that is found in association with the cellular cytoskeleton, that plays a role in maintaining or regulating the structural integrity of the cytoskeleton, or that mediates or regulates motile events mediated by the cytoskeleton. Includes cytoskeletal polymers (e.g., actin filaments, microtubules, intermediate filaments, myosin fragments), molecular motors (e.g., kinesins, myosins, dyneins), cytoskeleton associated regulatory proteins (e.g., tropomysin, alpha-actinin) and cytoskeletal associated binding proteins (e.g., microtubules associated proteins, actin binding proteins).

"Cytoskeletal function" refers to biological roles of the cytoskeleton, including but not limited to the providing of structural organization (e.g., microvilli, mitotic spindle) and the mediation of motile events within the cell (e.g., muscle contraction, mitotic chromosome movements, contractile ring formation and function, pseudopodal movement, active cell surface deformations, vesicle formation and translocation.)

A "diagnostic" as used herein is a compound, method, system, or device that assists in the identification and characterization of a health or disease state. The diagnostic can be used in standard assays as is known in the art.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"High stringency conditions" may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5× SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2× SSC (sodium chloride/sodium citrate) and 50% formamide at 55° C., followed by a high-stringency wash consisting of 0.1× SSC containing EDTA at 55° C.

"High throughput screening" as used herein refers to an assay which provides for multiple candidate agents or samples to be screened simultaneously. As further described below, examples of such assays may include the use of microtiter plates which are especially convenient because a large number of assays can be carried out simultaneously, using small amounts of reagents and samples.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, or plant cells. Both primary cells and cultured cell lines are included in this definition.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. Typically, stringent conditions will be those in which the salt concentration is less than about 1.0 M sodium ion, typically about 0.05 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The terms "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. Preferably, the percent identity exists over a region of the sequence that is at least about 25 amino acids in length, more preferably over a region that is at least 50 amino acids in length. This definition also refers to the reverse complement of a test nucleic acid sequence, provided that the test sequence has a designated or substantial identity to a reference sequence. Preferably, the percent identity exists over a region of the sequence that is at least about 25 nucleotides in length, more preferably over a region that is at least 50 nucleotides in length.

When percentage of sequence identity is used in reference to proteins or peptides, it is recognized that residue positions that are not identical often differ by conservative amino acid substitutions, where amino acid residues are substituted for other amino acid residues with similar chemical properties (e.g, charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. The scoring of conservative substitutions can be calculated according to, e.g., the algorithm of Meyers & Millers, Computer Applic. Biol. Sci. 4:11–17 (1988)

The terms "isolated", "purified", or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In an isolated gene, the nucleic acid of interest is separated from open reading frames which flank the gene of interest and encode proteins other than the protein of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "label" is a composition detectable by spectroscopic, photochemical, biochemical, immunochemical, or chemical means. For example, useful labels include fluorescent proteins such as green, yellow, red or blue fluorescent proteins, radioisotopes such as $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radio-label into the peptide, and used to detect antibodies specifically reactive with the peptide).

A "labeled nucleic acid probe or oligonucleotide" is one that is bound, either covalently, through a linker, or through ionic, van der Waals, or hydrogen bonds to a label such that the presence of the probe may be detected by detecting the presence of the label bound to the probe.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5× SSC (150 mM NaCl, 15 mM trisodium citrate), 50 mM sodium phosphate (pH 7.6), 5× Denhardt's solution, 10% dextran sulfate, and 20 μg/mL denatured sheared salmon sperm DNA, followed by washing the filters in 1× SSC at about 37–50° C. The skilled artisan will recognize how to adjust the temperature, ionic strength, etc. as necessary to accommodate factors such as probe length and the like.

"Modulators," "inhibitors," and "activators of a target protein" refer to modulatory molecules identified using in vitro and in vivo assays for target protein activity. Such assays include ATPase activity, microtubule gliding, microtubule depolymerizing activity, and binding activity such as microtubule binding activity or binding of nucleotide analogs. Samples or assays that are treated with a candidate agent at a test and control concentration. The control concentration can be zero. If there is a change in target protein activity between the two concentrations, this change indicates the identification of a modulator. A change in activity, which can be an increase or decrease, is preferably a change of at least 20% to 50%, more preferably by at least 50% to 75%, more preferably at least 75% to 100%, and more preferably 150% to 200%, and most preferably is a change of at least 2 to 10 fold compared to a control. Additionally, a change can be indicated by a change in binding specificity or substrate.

"Molecular motor" refers to a molecule that utilizes chemical energy to generate mechanical force. According to one embodiment, the molecular motor drives the motile properties of the cytoskeleton.

The phrase "motor domain" refers to the domain of a target protein that confers membership in the kinesin superfamily of motor proteins as determined by alignment with the motor domain of true kinesin.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. For example, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260)2605–2608 (1985); Cassol et al. 1992; Rossolini et al. Mol. Cell. Probes 8:91–98 (1994)). The term nucleic acid is used interchangeably with gene, cDNA, and mRNA encoded by a gene.

"Nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, T, or U) or modified bases. In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. A target protein comprises a polypeptide demonstrated to have at least microtubule depolymerization activity and, preferably that also binds to an antibody selectively immnuoreactive with KinI-3 or whose sequence is derived from KinI-3. by mutagenesis and/or recombination. Amino acids may be referred to herein by either their commonly known one or three letter symbols. Nucleotides, likewise, may be referred to by their commonly accepted single-letter codes, i.e., the one-letter symbols recommended by the IUPAC-IUB.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA box element. A promoter also optionally includes distal enhancer or repressor elements which can be located as much as several thousand base pairs from the start site of transcription. A "constitutive" promoter is a promoter that is active under most environmental and developmental conditions. An "inducible" promoter is a promoter that is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding moieties typically have an affinity for one another of at least $10^6$ $M^{-1}$. Preferred antibodies for use in diagnostics or therapeutics often have high affinities such as $10^7$, $10^8$, $10^9$ or $10^{10}$ $M^{-1}$. Specific binding to an antibody under such conditions may require an antibody that is selected for its specificity for a particular protein. For example, antibodies raised to KinI-3 with the amino acid sequence encoded in SEQ ID NO:2 can be selected to obtain only those antibodies that are specifically immunoreactive with KinI-3 and not with other proteins, except for polymorphic variants, orthologs, alleles, and closely related homologues of KinI-3. This selection may be achieved by subtracting out antibodies that cross react with molecules, for example, such as C. elegans unc-104 and human KiflA. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

"Test composition" (used interchangeably herein with "candidate agent" and "test compound" and "test agent") refers to a molecule or composition whose effect on the interaction between one or more cytoskeletal components it is desired to assay. The "test composition" can be any molecule or mixture of molecules, optionally in a carrier.

A "therapeutic" as used herein refers to a compound which is believed to be capable of modulating the cytoskeletal system in vivo which can have application in either human or animal disease. Modulation of the cytoskeletal system would be desirable in a number of conditions including, but not limited to: abnormal stimulation of endothelial cells (e.g., atherosclerosis), solid and hematopoetic tumors and tumor metastasis, benign tumors, for example, hemangiomas, acoustic neuromas, neurofibromas, pyogenic granulomas, vascular malfunctions, abnormal wound healing, inflammatory and immune disorders such as rheumatoid arthritis, Bechet's disease, gout or gouty arthritis, abnormal angiogenesis accompanying: rheumatoid arthritis, psoriasis, diabetic retinopathy, and other ocular angiogenic disesase such as, macular degeneration, corneal graft rejection, corneal overgrowth, glaucoma, and Osler Webber syndrome.

II. The Target Protein

The present invention provides for the first time a nucleic acid encoding KinI-3. This protein is a member of the kinesin superfamily of motor proteins. More specifically, the KinI-3 sequence of FIG. 2 shares approximately 50% identity with various kinesins, being closest in sequence to the opossum protein MdKRP and to human MCAK. KinI-3 falls within a class of kinesins having internal motor domains; other kinesins have N-terminal motor domains.

In one aspect, KinI-3 can be defined by having at least one or preferably more than one of the following functional and structural characteristics. Functionally, KinI-3 has microtubule depolymerization activity and microtubule motor activity that is ATP dependent. KinI-3 activity can also be described in terms of its ability to bind microtubules.

The novel nucleotides sequences provided herein encode KinI-3 or fragments thereof. Thus, in one aspect, the nucleic acids provided herein are defined by the novel proteins provided herein. The protein provided herein comprises an amino acid sequence which has one or more of the following characteristics: greater than 70% sequence identity with SEQ ID NO:2, or the motor domain thereof, preferably greater than 80%, more preferably greater than 90%, more preferably greater than 95% or, in another embodiment, has 98 to 100% sequence identity with SEQ ID NO:2. As described above, when describing the nucleotide in terms of SEQ ID NO:1 or SEQ ID NOS:3, 5, 7 or 9, the sequence identity can be the same percentages or slightly lower due to the degeneracy in the genetic code. The invention also includes fragments of nucleotide sequence shown in FIG. 1 having at least 10, 15, 20, 25, 50, 100, 1000 or 2000 contiguous nucleotides from SEQ ID NO:1 or a degenerate form thereof. Some fragments include the motor domain which occurs approximately between positions I224 to E545 of the amino acid sequence in FIG. 2 (determined by sequence comparison of the motor domain of other kinesins). Some such fragments can be used as hybridization probes or primers. Unless otherwise apparent from the context, reference to nucleotide sequences shown in the Figures or sequence can refer to the sequence shown, its perfect complement or a duplex of the two strands. Also included within the definition of the target proteins are amino acid sequence variants of wild-type target proteins.

Portions of the KinI-3 nucleotide sequence may be used to identify polymorphic variants, orthologs, alleles, and homologues of KinI-3. This identification can be made in vitro, e.g., under stringent hybridization conditions and sequencing, or by using the sequence information in a computer system for comparison with other nucleotide sequences. Sequence comparison can be performed using any of the sequence comparison algorithms discussed below, with BLAST as a preferred algorithm.

As will be appreciated by those in the art, the target proteins can be made in a variety of ways, including both synthesis de novo and by expressing a nucleic acid encoding the protein.

Target proteins of the present invention may also be modified in a way to form chimeric molecules comprising a fusion of a target protein with a tag polypeptide which provides an epitope to which an anti-tag antibody can selectively bind. The epitope tag is generally placed at the amino or carboxyl terminus of the target protein. Provision of the epitope tag enables the target protein to be readily detected, as well as readily purified by affinity purification. Various tag epitopes are well known in the art. Examples include poly-histidine (poly-his) or poly-histidine-glycine (poly-his-gly) tags; the flu HA tag polypeptide and its antibody 12CA5 (see, Field et al. (1988) Mol. Cell. Biol. 8:2159); the c-myc tag and the 8F9, 3C7, 6E10, G4, B7 and 9E10 antibodies thereto (see, Evans et al., (1985) Molecular and Cellular Biology, 5:3610); and the Herpes Simplex virus glycoprotein D (gD) tag and its antibody (see, Paborsky et al., (1990) Protein Engineering, 3:547). Other tag polypeptides include the Flag-peptide (see, Hopp et al. (1988) BioTechnology 6:1204); the KT3 epitope peptide (see, Martine et al. (1992) Science, 255:192); tubulin epitope peptide (see, Skinner (1991) J. Biol. Chem. 266:15173); and the T7 gene 10 protein peptide tag (see, Lutz-Freyermuth et al. (1990) Proc. Natl. Acad. Sci. USA 87:6393.

The biological activity of any of the peptides provided herein can be routinely confirmed by the assays provided herein such as those which assay ATPase activity or microtubule binding activity. In one embodiment, polymorphic variants, alleles, and orthologs, homologues of KinI-3 are confirmed by using a ATPase or microtubule binding assays as known in the art.

The isolation of biologically active KinI-3 for the first time provides a means for assaying for modulators of this kinesin superfamily protein. Biologically active KinI-3 is useful for identifying modulators of KinI-3 or fragments thereof and kinesin superfamily members using in vitro assays such as microtubule gliding assays, ATPase assays (Kodama et al., *J. Biochem.* 99:1465–1472 (1986); Stewart et al., *Proc. Nat'l Acad. Sci. USA* 90:5209–5213 (1993)), and binding assays including microtubule binding assays (Vale et al., *Cell* 42:39–50 (1985)). In vivo assays and uses are provided herein as well. Also provided herein are methods of identifying candidate agents which bind to KinI-3 and portions thereof.

Some portions or fragments of KinI-3 include at least 7, 10, 15, 20, 35, 50, 100, 250, 300, 350, 500, or 1000 contiguous amino acids from the sequence shown in FIG. 2. Some fragments contain fewer than 1000, 500, 250, 100 or 50 contiguous amino acids from the sequence shown in FIG. 2. For example, exemplary fragments include fragments having 15–50 amino acids or 100–500 amino acids. Some fragments include a motor domain. The motor domain begins between amino acids 210–240 and runs to amino acids about 530–560. The motor domain in FIG. 2 runs from I224 to E545 determined by sequence identity to other kinesins. Some fragments include a ligand binding domain of KinI-3. Nucleic acids encoding such fragments are also included in the invention. The nucleic acid coordinates corresponding to the 1224 to E545 fragment are 670 to 1635 with the A in the initiating ATG codon numbered 1.

As further described herein, a wide variety of assays, therapeutic and diagnostic methods are provided herein which utilize the novel compounds described herein. The uses and methods provided herein, as further described below have in vivo, in situ, and in vitro applications, and can be used in medicinal, veterinary, agricultural and research based applications.

III. Isolation of the Gene Encoding KinI-3

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)), Methods in Enzymology Vol 266 (R. F. Doolittle, ed., 1996).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from mass spectroscopy, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 225:137–149 (1983).

The sequence of the cloned genes and synthetic oligonucleotides can be verified after cloning using, e.g., the chain termination method for sequencing double-stranded templates of Wallace et a., *Gene* 16:21–26 (1981).

B. Cloning Methods for the Isolation of Nucleotide Sequences Encoding KinI-3

In general, the nucleic acid sequences encoding KinI-3 and related nucleic acid sequence homologs are cloned from cDNA and genomic DNA libraries or isolated using amplification techniques with oligonucleotide primers. Alternatively, expression libraries can be used to clone KinI-3 and KinI-3 homologues by detected expressed homologues immunologically with antisera or purified antibodies made against KinI-3 that also recognize and selectively bind to the KinI-3 homologue. Finally, amplification techniques using primers can be used to amplify and isolate KinI-3 from DNA or RNA. Amplification techniques using degenerate primers can also be used to amplify and isolate KinI-3 homologues. Amplification techniques using primers can also be used to isolate a nucleic acid encoding KinI-3. These primers can be used, e.g., to amplify a probe of several hundred nucleotides, which is then used to screen a library for full-length KinI-3.

Appropriate primers and probes for identifying the gene encoding homologues of KinI-3 in other species are generated from comparisons of the sequences provided herein. As described above, antibodies can be used to identify KinI-3 homologues. For example, antibodies made to the motor domain of KinI-3 or to the whole protein are useful for identifying KinI-3 homlogs.

To make a cDNA library, one should choose a source that is rich in the mRNA of choice, e.g., KinI-3. For example, KinI-3 mRNA is most abundant in peripheral blood lymphocytes and bone marrow, with relatively lower levels of expression in colon, lung, small intestine, skin, placenta, and fetal liver. See, FIGS. 3 and 4. The mRNA is then made into cDNA using reverse transcriptase, ligated into a recombinant vector, and introduced into a recombinant host for propagation, screening and cloning. Methods for making and screening cDNA libraries are well known (see, e.g., Gubler & Hoffman, *Gene* 25: 263–269); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is read out as generally described in Grunstein et al., *Proc. Natl. Acad. Sci. USA*, 72:3961–3965 (1975).

An alternative method of isolating KinI-3 nucleic acid and its homologues combines the use of synthetic oligonucleotide primers and amplification of an RNA or DNA template (see U.S. Pat. Nos. 4,683,195 and 4,683,202; PCR Protocols: A guide to Methods and Applications (Innis et al., eds. 1990)). Methods such as polymerase chain reaction and ligase chain reaction can be used to amplify nucleic acid sequences of KinI-3 directly from mRNA, from cDNA, from genomic libraries or cDNA libraries. Degenerate oligonucleotides can be designed to amplify KinI-3 homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of KinI-3 encoding mRNA in physiological samples, for nucleic sequencing or for other purposes. Genes amplified by the PCR reaction can be purified from agarose gels and cloned into an appropriate vector.

Gene expression of KinI-3 can also be analyzed by techniques known in the art, e.g., reverse transcription and amplification of mRNA, isolation of total RNA or poly A+RNA, northern blotting, dot blotting, in situ hybridization, RNase protection, quantitative PCR, and the like.

Synthetic oligonucleotides can be used to construct recombinant KinI-3 genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the KinI-3 gene. The specific subsequence is then ligated into an expression vector.

The gene for KinI-3 is typically cloned into intermediate vectors before transformation into prokaryotic or eukaryotic cells for replication and/or expression. The intermediate vectors are typically prokaryote vectors or shuttle vectors.

C. Expression in Prokaryotes and Eukaryotes

To obtain high level expression of a cloned gene, such as those cDNAs encoding KinI-3, it is important to construct an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the KinI-3 protein are available in, e.g., *E. coli*, Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. The pET expression system (Novagen) is a preferred prokaryotic expression system.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the KinI-3 encoding nucleic acid in host cells. A typical expression cassette thus contains a promoter operably linked to the nucleic acid sequence encoding KinI-3 and signals required for efficient polyadenylation of the transcript, ribosome binding sites, and translation termination. The nucleic acid sequence encoding KinI-3 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23, and fusion expression systems such as GST and LacZ. Epitope tags can also be added to recombinant proteins to provide convenient methods of isolation, e.g., c-myc or histidine tags.

Expression vectors containing regulatory elements from eukaryotic viruses are typically used in eukaryotic expression vectors, e.g., SV40 vectors, cytomegalovirus vectors, papilloma virus vectors, and vectors derived from Epstein Bar virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 late promoter, CMV promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a KinI-3 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection or transformation methods are used to produce bacterial, mammalian, yeast or insect cell lines that express large quantities of KinI-3 protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher ed., 1990)).

Transformation of eukaryotic and prokaryotic cells are performed according to standard techniques (see, e.g., Morrison, *J. Bact.*, 132:349–351 (1977); Clark-Curtiss & Curtiss, *Methods in Enzymology*, 101:347–362 (Wu et al., eds, 1983). Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing KinI-3.

After the expression vector is introduced into the cells, the transfected cells are cultured under conditions favoring expression of KinI-3, which is recovered from the culture using standard techniques identified below.

IV. Purification of KinI-3 Protein

Either naturally occurring or recombinant KinI-3 can be purified for use in functional assays. In a preferred embodiment, the target proteins are purified for use in the assays to provide substantially pure samples. Alternatively, the target protein need not be substantially pure as long as the sample comprising the target protein is substantially free of other components that can contribute to the production of ADP or phosphate.

The target proteins may be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography, chromatofocussing, selective precipitation with such substances as ammonium sulfate; and others (see, e.g., Scopes, Protein Purification: Principles and Practice (1982); U.S. Pat. No. 4,673,641; Ausubel et al. supra; and Sambrook et al., supra). For example, the target protein can be purified using a standard anti-target antibody column. Ultrafiltration and diafiltration techniques, in conjunction with protein concentration, are also useful. A preferred method of purification is use of Ni-NTA agarose (Qiagen).

The expressed protein can be purified by standard chromatographic procedures to yield a purified, biochemically active protein. The activity of any of the peptides provided herein can be routinely confirmed by the assays provided herein such as those which assay microtubule depolymerization activity or microtubule binding activity. Biologically active target protein is useful for identifying modulators of target protein or fragments thereof and kinesin superfamily members using in vitro assays such as microtubule gliding assays, depolymerization assays, and ATPase assays (Kodama et al., J. Biochem. 99:1465–1472 (1986); Stewart et al., Proc. Nat'l Acad. Sci. USA 90:5209–5213 (1993)), and binding assays including microtubule binding assays (Vale et al., Cell 42:39–50 (1985)), as described in detail below.

A. Purification of KinI-3 from Recombinant Bacteria

Recombinant proteins are expressed by transformed bacteria in large amounts, typically after promoter induction; but expression can be constitutive. Promoter induction with IPTG is a preferred method of expression. Bacteria are grown according to standard procedures in the art. Fresh or frozen bacteria cells are used for isolation of protein. Alternatively, it is possible to purify KinI-3 from bacteria periplasm. After KinI-3 is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Suitable purification schemes for some specific kinesins are outlined in U.S. Ser. No. 09/295,612, filed Apr. 20, 1999, hereby expressly incorporated herein in its entirety for all purposes.

B. Standard Protein Separation Techniques For Purifying KinI-3 Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of KinI-3 can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

KinI-3 can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of KinI-3

In addition to the detection of KinI-3 genes and gene expression using nucleic acid hybridization technology, one can also use immunoassays to detect KinI-3. Immunoassays can be used to qualitatively or quantitatively analyze KinI-3. A general overview of the applicable technology can be found in Harlow & Lane, *Antibodies: A Laboratory Manual* (1988).

A. Antibodies to KinI-3

Methods of producing polyclonal and monoclonal antibodies that react specifically with KinI-3 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or 10 mice (see, e.g., Huse et al., *Science* 246:1275–1281 (1989); Ward et al., *Nature* 341:544–546 (1989)).

Humanized forms of mouse antibodies can be generated by linking the CDR regions of non-human antibodies to human constant regions by recombinant DNA techniques. See Queen et al., Proc. Natl. Acad. Sci. USA 86, 10029–10033 (1989) and WO 90/07861 (incorporated by reference for all purposes).

Human antibodies can be obtained using phage-display methods. See, e.g., Dower et al., WO 91/17271; McCafferty et al., WO 92/01047. In these methods, libraries of phage are produced in which members display different antibodies on their outersurfaces. Antibodies are usually displayed as Fv or Fab fragments. Phage displaying antibodies with a desired specificity are selected by affinity enrichment to KinI-3 or fragments thereof. Human antibodies against KinI-3 can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991) (each of which is incorporated by reference in its entirety for all purposes). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from human immunized with an immunogenic agent. Optionally, such polyclonal antibodies can be concentrated by affinity purification using KinI-3 as an affinity reagent.

A number of KinI-3 comprising immunogens may be used to produce antibodies specifically reactive with KinI-3. For example, recombinant KinI-3 or a antigenic fragment thereof such as the motor domain, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to KinI-3. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-KinI-3 proteins or even other homologous proteins from other organisms (e.g., *C. elegans* unc-104 or human Kifl A), using a competitive binding immunoassay. Specific polyclonal antisera and monoclonal antibodies will usually bind with a $K_d$ of at least about 0.1 mM, more usually at least about 1 μM, preferably at least about 0.1 μM or better, and most preferably, 0.01 μM or better.

Once KinI-3 specific antibodies are available, KinI-3 can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio ed., 1980); and Harlow & Lane, supra.

B. Binding Assays

Antibodies can be used for treatment or to identify the presence of KinI-3 having the sequence identity characteristics as described herein. Additionally, antibodies can be used to identify modulators of the interaction between the antibody and KinI-3 as further described below. While the following discussion is directed toward the use of antibodies in the use of binding assays, it is understood that the same general assay formats such as those described for "non-competitive" or "competitive" assays can be used with any compound which binds to KinI-3 such as microtubules or the compounds described in Ser. No. 60/070,772.

In a preferred embodiment, KinI-3 is detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology* (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the KinI-3 or antigenic subsequence thereof). The antibody (e.g., anti-KinI-3) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled KinI-3 polypeptide or a labeled anti-KinI-3 antibody. Alternatively, the labeling agent may be a third moiety, such a secondary antibody, that specifically binds to the antibody/KinI-3 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see generally Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 4° C. to 40° C.

Non-Competitive Assay Formats

Immunoassays for detecting KinI-3 in samples may be either competitive or noncompetitive. Noncompetitive immunoassays are assays in which the amount of antigen is directly measured. In one preferred "sandwich" assay, for example, the anti-KinI-3 antibodies can be bound directly to a solid substrate on which they are immobilized. These immobilized antibodies then capture KinI-3 present in the test sample. KinI-3 is thus immobilized is then bound by a labeling agent, such as a second KinI-3 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of KinI-3 present in the sample is measured indirectly by measuring the amount of a known, added (exogenous) KinI-3 displaced (competed away) from an anti-KinI-3 antibody by the unknown KinI-3 present in a sample. In one competitive assay, a known amount of KinI-3 is added to a sample and the sample is then contacted with an antibody that specifically binds to KinI-3. The amount of exogenous KinI-3 bound to the antibody is inversely proportional to the concentration of KinI-3 present in the sample. In a particularly preferred embodiment, the antibody is immobilized on a solid substrate. The amount of KinI-3 bound to the antibody may be determined either by measuring the amount of KinI-3 present in a KinI-3/antibody complex, or alternatively by measuring the amount of remaining uncomplexed protein. The amount of KinI-3 may be detected by providing a labeled KinI-3 molecule.

A hapten inhibition assay is another preferred competitive assay. In this assay the known KinI-3, is immobilized on a solid substrate. A known amount of anti-KinI-3 antibody is added to the sample, and the sample is then contacted with the KinI-3. The amount of anti-KinI-3 antibody bound to the known immobilized KinI-3 is inversely proportional to the amount of KinI-3 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a protein at least partially encoded by SEQ ID NO:2 can be immobilized to a solid support. Proteins (e.g., C. elegans unc-104 or human KiflA) are added to the assay that compete for binding of the antisera to the immobilized antigen. The ability of the added proteins to compete for binding of the antisera to the immobilized protein is compared to the ability of KinI-3 encoded by SEQ ID NO:2 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologues.

The immunoabsorbed and pooled antisera are then used in a competitive binding immunoassay as described above to compare a second protein, thought to be perhaps the protein of this invention, to the immunogen protein (i.e., KinI-3 of SEQ ID NO:2). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 that is required to inhibit 50% of binding, then the second protein is said to specifically bind to the polyclonal antibodies generated to a KinI-3 immunogen.

Other Assay Formats

Western blot (immunoblot) analysis is used to detect and quantify the presence of KinI-3 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind KinI-3. The anti-KinI-3 antibodies specifically bind to the KinI-3 on the solid support. These antibodies may be directly labeled or alternatively may be subsequently detected using labeled antibodies (e.g., labeled sheep anti-mouse antibodies) that specifically bind to the anti-KinI-3 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), colorimetric labels such as colloidal gold or colored glass or plastic beads (e.g., polystyrene, polypropylene, latex, etc.) or other labels that can be detected by mass spectroscopy, NMR spectroscopy, or other analytical means known in the art.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize KinI-3, or secondary antibodies that recognize anti-KinI-3.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of the Target Protein

A. Functional Assays

The activity of biologically active KinI-3 and compounds that modulate this activity can be assessed using a variety of in vitro or in vivo assays known in the art, e.g., ATPase, microtubule gliding, and microtubule binding, microtubule depolymerization assays (Kodama et al., J. Biochem. 99: 1465–1472 (1986); Stewart et al., Proc. Nat'l Acad. Sci. USA 90: 5209–5213 (1993); (Lombillo et al., J. Cell Biol. 128:107–115 (1995); (Vale et al., Cell 42:39–50 (1985)). Methods of performing motility assays are well known (see, e.g., Hall, et al. (1996), Biophys. J., 71: 3467–3476, Turner et al., 1996, Anal. Biochem. 242 (1):20–5; Gittes et al., 1996, Biophys. J. 70(1): 418–29; Shirakawa et al., 1995, J. Exp. Biol. 198: 1809–15; Winkelmann et al., 1995, Biophys. J. 68: 2444–53; Winkelmann et al., 1995, Biophys. J. 68: 72S, and the like). A preferred assay that monitors depolymerization of microtubules to tubulin is described in the Examples. Activity of a modulator is shown by increasing or decreasing the intensity of the tubulin band as described in the Examples. Alternatively, the assay can be performed using fluorescently labelled microtubules, and changes in fluorescent monitored as the microtubules depolymerizes. Depolymerization usually results in a change in fluorescence, typically a decrease. For example, the fluorescence intensity of thedye DAPI is higher when bound to microtubules than subunits thereof (see Hartman et al. Cell 93, 277–287 (1998)). Alternatively, depolymerization can be monitored by imaging to detect a change in location of fluorescent label. Fluorescence detection formats are particularly suitable for high throughput screening.

Such assays can be used to test for the activity of KinI-3 isolated from endogenous sources or recombinant sources. Furthermore, such assays can be used to test for modulators of KinI-3. Modulators can increase or decrease activity of KinI-3. Some modulators identified by such assays are specific for KinI-3, whereas other modulators also modulate other kinesins showing substantial sequence identity with KinI-3. In some applications requiring selective modulation of KinI-3, modulators specific for KinI-3 are advantageous. In other applications, modulators that simultaneously modulate a family of related kinesins are advantageous.

Molecular motor activity can also be measured by the methods disclosed in Ser. No. 09/314,464, filed May 18, 1999, entitled "Compositions and assay utilizing ADP or phosphate for detecting protein modulators", which is incorporated herein by reference in its entirety. More specifically, this assay detects modulators of any aspect of a kinesin motor function ranging from interaction with microtubules to hydrolysis of ATP. ADP or phosphate is used as the readout for protein activity.

There are a number of enzymatic assays known in the art which use ADP as a substrate. For example, kinase reactions such as pyruvate kinases are known. See, Nature 78:632 (1956) and Mol. Pharmacol. 6:31 (1970). This is a preferred method in that it allows the regeneration of ATP. In one embodiment, the level of activity of the enzymatic reaction is determined directly. In a preferred embodiment, the level of activity of the enzymatic reaction which uses ADP as a substrate is measured indirectly by being coupled to another reaction. For example, in one embodiment, the method further comprises a lactate dehydrogenase reaction under conditions which normally allow the oxidation of NADH, wherein said lactate dehydrogenase reaction is dependent on the pyruvate kinase reaction. Measurement of enzymatic reactions by coupling is known in the art. Furthermore, there are a number of reactions which utilize phosphate. Examples of such reactions include a purine nucleoside phosphorylase reaction. This reaction can be measured directly or indirectly. A particularly preferred embodiments utilizes the pyruvate kinase/lactate dehydrogenase system.

In one embodiment, the detection of the ADP or phosphate proceeds non-enzymatically, for example, by binding or reacting the ADP or phosphate with a detectable compound. For example, phosphomolybdate based assays may be used which involve conversion of free phosphate to a phosphomolybdate complex. One method of quantifying the phosphomolybdate is with malachite green. Alternatively, a fluorescently labeled form of a phosphate binding protein, such as the E. coli phosphate binding protein, can be used to measure phosphate by a shift in its fluorescence.

In addition, target protein activity can be examined by determining modulation of target protein in vitro using cultured cells. The cells are treated with a candidate agent and the effect of such agent on the cells is then determined either directly or by examining relevant surrogate markers. For example, characteristics such as mitotic spindle morphology and cell cycle distribution can be used to determine the effect.

Thus, in a preferred embodiment, the methods comprise combining a target protein and a candidate agent, and determining the effect of the candidate agent on the target protein. Generally a plurality of assay mixtures are run in parallel with different agent concentrations to obtain a differential response to the various concentrations. Typically, one of these concentrations serves as a negative control, i.e., at zero concentration or below the level of detection.

As will be appreciated by those in the art, the components may be added in buffers and reagents to assay target protein activity and give optimal signals. Since the methods allow kinetic measurements, the incubation periods can be optimized to give adequate detection signals over the background.

In a preferred embodiment, an antifoam or a surfactant is included in the assay mixture. Suitable antifoams include, but are not limited to, antifoam 289 (Sigma). Suitable surfactants include, but are not limited to, Tween, Tritons, including Triton X-100, saponins, and polyoxyethylene ethers. Generally, the antifoams, detergents, or surfactants are added at a range from about 0.01 ppm to about 10 ppm.

A preferred assay design is also provided. In one aspect, the invention provides a multi-time-point (kinetic) assay, with at least two data points being preferred. In the case of multiple measurements, the absolute rate of the protein activity can be determined.

B. Binding Assays

In a preferred embodiment, the binding of the candidate agent is determined through the use of competitive binding assays. In this embodiment, the competitor is a binding moiety known to bind to the target protein, such as an antibody, peptide, binding partner, ligand, etc. Under certain circumstances, there may be competitive binding as between the candidate agent and the binding moiety, with the binding moiety displacing the candidate agent.

Competitive screening assays may be done by combining the target protein and a drug candidate in a first sample. A second sample comprises a candidate agent, the target protein and a compound that is known to modulate the target protein. This may be performed in either the presence or absence of microtubules. The binding of the candidate agent is determined for both samples, and a change, or difference in binding between the two samples indicates the presence of an agent capable of binding to the target protein and potentially modulating its activity. That is, if the binding of the candidate agent is different in the second sample relative to the first sample, the candidate agent is capable of binding to the target protein.

In one embodiment, the candidate agent is labeled. Either the candidate agent, or the competitor, or both, is added first to the target protein for a time sufficient to allow binding. Incubations may be performed at any temperature which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to the target protein and thus is capable of binding to, and potentially modulating, the activity of the target protein. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to the target protein with a higher affinity. Thus, if the candidate agent is labeled, the presence of the label on the support, coupled with a lack of competitor binding, may indicate the candidate agent is capable of binding to the target protein.

C. Candidate Agents

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. In a preferred embodiment, the candidate agents are organic chemical moieties, a wide variety of which are available in the literature.

Combinatorial libraries can be produced for many types of compounds that can be synthesized in a step-by-step fashion. Such compounds include polypeptides, proteins, nucleic acids, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of compounds can be constructed by the encoded synthetic libraries (ESL) method described in Affymax, WO 95/12608, Affymax WO 93/06121, Columbia University, WO 94/08051, Pharmacopeia, WO 95/35503 and Scripps, WO 95/30642 (each of which is incorporated herein by reference in its entirety for all purposes). Peptide libraries can also be generated by phage display methods. See, e.g., Devlin, WO 91/18980. Compounds to be screened can also be obtained from governmental or private sources, including, e.g., the National Cancer Institute's (NCI) Natural Product Repository, Bethesda, Md., the NCI Open Synthetic Compound Collection, Bethesda, Md., NCI's Developmental Therapeutics Program, or the like. Compounds to be screened can also be obtained from governmental or private sources, including, e.g., the National Cancer Institute's (NCI) Natural Product Repository, Bethesda, Md., the NCI Open Synthetic Compound Collection, Bethesda, Md., NCI's Developmental Therapeutics Program, or the like.

D. Other Assay Components

The assays provided utilize target protein as defined herein. In one embodiment, portions of target protein are utilized; in a preferred embodiment, portions having target protein activity as described herein are used. In addition, the assays described herein may utilize either isolated target proteins or cells or animal models comprising the target proteins.

A variety of other reagents may be included in the screening assays. These include reagents like salts, neutral proteins, e.g. albumin, detergents, etc which may be used to facilitate optimal protein-protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding.

VII. Applications

The methods of the invention are used to identify compounds useful in the treatment of cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compositions and methods provided herein are particularly deemed useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nepbroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma, pinealoma, glioblastoma multiform, oligodendroglioma, schwannoma, retinoblastoma, congenital tumors), spinal cord neurofibroma, meningioma, glioma, sarcoma; Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Accordingly, the compositions of the invention are administered to cells. By "administered" herein is meant administration of a therapeutically effective dose of the candidate agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant almost any cell in which mitosis or meiosis can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Candidate agents having the desired pharmacological activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1–100 wt. %. The agents maybe administered alone or in combination with other treatments, i.e., radiation, or other chemotherapeutic agents.

In a preferred embodiment, the pharmaceutical compositions are in a water soluble form, such as pharmaceutically acceptable salts, which is meant to include both acid and base addition salts.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations. The administration of the candidate agents of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the candidate agents may be directly applied as a solution or spray.

The methods described herein also can be used for diagnostic applications. A diagnostic as used herein is a compound or method that assists in the identification and characterization of a health or disease state in humans or other animals.

The present invention also provides for kits for screening for modulators of the target protein. Such kits can be prepared from readily available materials and reagents. For example, such kits can comprise any one or more of the following materials: biologically active target protein, reaction tubes, and instructions for testing activity of the target protein. Preferably, the kit contains biologically active target protein. A wide variety of kits and components can be prepared according to the present invention, depending upon the intended user of the kit and the particular needs of the user. For example, the kit can be tailored for microtubule depolymerization assays, ATPase assays, microtubule gliding assays, or microtubule binding assays. KinI-3's microtubule motor activity makes it useful for a variety of other applications. The kinesins of the present invention and in particular their motor domains can be used for separation of a specific ligand from a heterologous mixtures in aqueous solution as described by Stewart (U.S. Pat. No. 5,830,659). In the system discussed by Stewart, a kinesin motor domain is linked to a ligand binding moiety, such as streptavidin. The chimeric kinesin motor domains are placed into a loading chamber containing the heterogeneous mixtures which is coupled to a receiving chamber by a channel bearing immobilized, aligned microtubules. Addition of ATP to the loading chamber results in translocation of the kinesin motor domains, now attached non-covalently to the desired ligand via their ligand binding moiety, from the loading chamber to the receiving chamber. Hence, the ATP-driven motility activity of the kinesin motor domain results in separation of the desired ligand from the heterogeneous mixture. According to Stewart, all kinesin motor domains are suitable for use in the separation system.

The kinesins of the invention and in particular their motor domains can also be used in nanotechnological applications. In general, the ability to convert chemical energy to linear force exerted upon a microtubule substrate is useful in the design of nanoscale switching devices and nanometer scale rotary devices (see Korngruth, *Nanotechnology and Biomolecular Electronics*, National Institute of Standards and Technology White Paper). Kinesin motor domains may be used in the construction of rotors and other mechanical components (for review see Limberis and Stewart, *Nanotechnology* 11:47–51 (2000)); by linking ATP synthesis to a photosynthetic process, kinesin motor domains may be employed as light-operated molecular shuttles useful for nanoscale switches and pumps (see Dennis et al., *Nanotechnology* 10:232–236 (1999)). Additional applications include cascaded biomolecular linearmiotoric motility systems, wherein a microtubule stator and kinesin slide are utilized in the design of an actuator (see Stracke et al., *Nanotechnology* 11:52–56 (2000)) and linear analysis of polymers (see U.S. Pat. No. 6,210,896).

Nucleic acids encoding the kinesins of the invention are also useful for inclusion on a GeneChip™ array or the like for use in expression monitoring (see U.S. Pat. No. 6,040,138, EP 853, 679 and WO97/27317). Such arrays typically contain oligonucleotide or cDNA probes to allow detection of large numbers of mRNAs within a mixture. Many of the nucleic acids included in such arrays are from genes or ESTs that have not been well characterized. Such arrays are often used to compare expression profiles between different tissues or between different conditions of the same tissue (healthy vs. diseased or drug-treated vs. control) to identify differentially expressed transcripts. The differentially expressed transcripts are then useful e.g., for diagnosis of disease states, or to characterize responses of drugs. The nucleic acids of the invention can be included on Gene-Chip™ arrays or the like together with probes containing a variety of other genes. The present nucleic acids are particularly useful for inclusion in GeneChip™ arrays for analyzing the cell cycle or proliferation state of cells. Nucleic acids encoding KinI-3 can be combined with nucleic acids encoding other kinesin molecules and/or nucleic acids from other genes having roles in DNA replication, cell division or other cell cycle function. Such arrays are useful for analyzing and diagnosing cells in a proliferating state, and diseases such as cancer characterized by presence of the same. Such arrays are also useful for analyzing candidate drugs for roles in modulation of the cell cycle and proliferation. The efficacy of such drugs can be assayed by determining the effect of the drug on the expression profile of genes affecting proliferation and the cell cycle.

VIII. Examples

1. Motor Activity

A number of constructs containing all or part of the motor domain were tested for ATPase activity and microtubule depolymerase activity.

Bacterially expressed and purified KinI-3 protein was assayed for its microtubule-stimulated ATP-ase activity in a reaction buffer composed of 40 uM MES/KOH pH6.8, 2 mM MgCl2, 1 mM DTT,1 mM EGTA, 100 uM ATP, 10 uM paclitaxel, 0.1 mg/mlBSA, 0.5 mM NADH, 1.5 mM phosphoenolpyruvate, lactate dehydrogenase/pyruvate kinase mix (Sigma, diluted 1:200 v/v final) and varied amounts of microtubules (from 50 ug/ml to 24 ng/ml). The reaction progress was followed up over time by monitoring absorbance of the reaction mix at 340 nm using microtiter plate reader (SpectraMAX340, Molecular Devices Inc.) The rate of the absorbance change was converted to uM NADH oxidized per second by referencing it to a set of standard NADH solutions of known concentrations. In this coupled ATPase assay conversion of one NADH to NAD+ reports appearance of one ADP molecule, and as such reports a single turnover of ATPase.

For the microtubule depolymerase, reaction mixes were assembled according to the table below. ADP, AMPPNP and Apyrase mixtures were included as negative controls. Samples were incubated at room temperature for 15 min. Samples were centrifuged at 100000 g for 10 min. Supernatant was aspirated away from the microtubule pellet and mixed with an equal volume of 2× SDSPAGE loading dye. Pellet was resuspended in a volume of 1× loading dye equivalent to 2× starting volume of the sample before spin. Both supernatant and pellet samples were loaded on an SDS PAGE gel, run and stained with Coomassie Blue according to standard procedures. Appearance of tubulin (about 50 kDa) in the lanes containing the supernatant was interpreted as a sign of microtubule depolymerization

| Construct | ATPase activity | MT depolymerization |
|---|---|---|
| E213/L546 | undetectable | yes |
| E213/S566 | undetectable | weak |
| E233F541 | undetectable | no |

The observation that KinI-3 catalyzed microtubule depolymerization in the presence of ATP, but not ADP or AMP-PNP or Apyrase indicates that the depolymerization was dependent on the presence of hydrolysable ATP. Therefore, it is likely that KinI-3 does have a low level of ATPase activity even though this was not detected in the ATPase assay performed as described above.

2. Expression Profile

A real time quantitative PCR assay (TaqMan™, Applied Biosystems) was developed specifically to measure KinI-3 mRNA levels in human tissues and cell lines in order to assess the biological function of KinI-3. Previous studies have shown that kinesins involved in mitosis such as human KSP are upregulated in tumor versus normal tissue and that their expression is correlated with the proliferation index of cells. Conversely, the expression level of kinesins not involved in mitosis is not correlated with proliferation or mitotic index.

Figure 8:
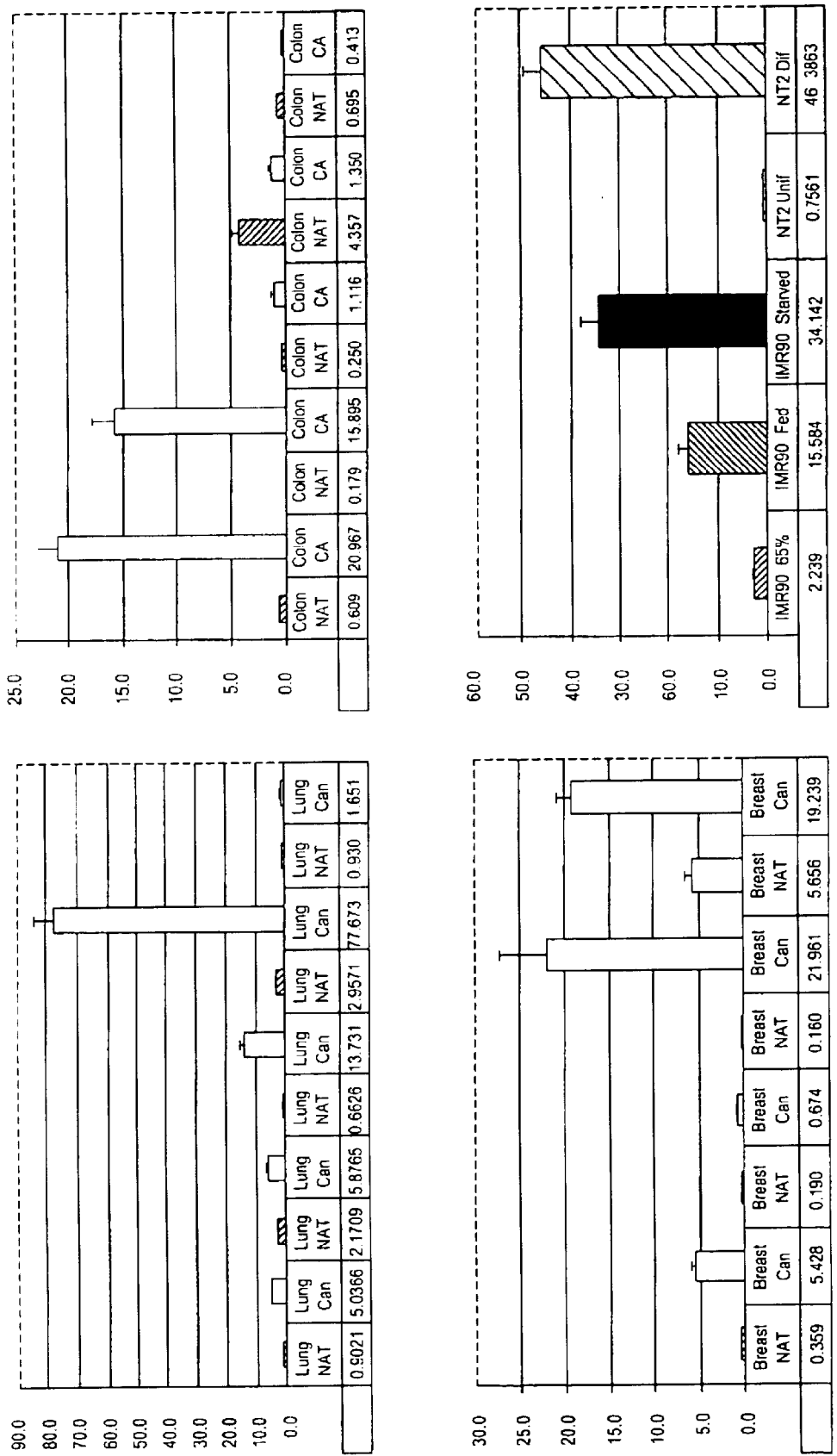
FIG. 8 shows the expression of KinI-3 in a variety of tissues, both normal (wherein "NAT" refers to normal adjacent tissue) and diseased (wherein "CA" or "Can" refers to cancerous cells), and in a neuronal model (NT-2 cells, wherein "Undif." refers to undifferentiated cells and "Dif." refers to differentiated cells). The values are normalized to the expression of an housekeeping gene (GUS) and compared to the expression in HeLa cells (a relative expression of 1 means the same level of expression as in HeLa).
Figure 9:
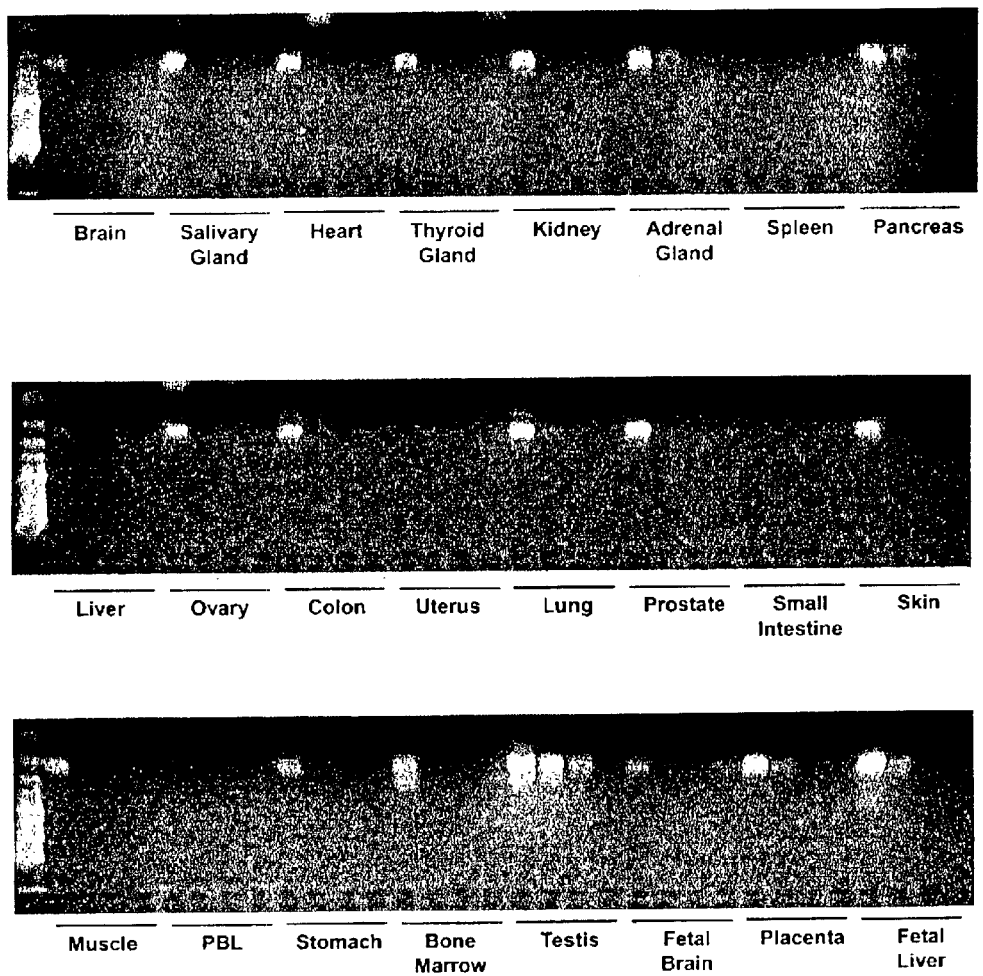
FIG. 9 shows the qualitative tissue expression profile of AL363662 in a variety of tisues.

The expression profile of KinI-3 in various cells tissues is shown in FIG. 8. Abbreviations are as follows:

CAN: cancer

NAT: Normal Adjacent Tissue

| | 1 MT only | 2 AL only | 3 AL + ATP/MT | 4 AL (treated by Apyrase) + MT | 5 AL + MT/AMPPNP | 6 AL + MT + ADP | Final Conc. |
|---|---|---|---|---|---|---|---|
| MT (1.6 mg/ml)(ul) | 100 | 0 | 100 | 100 | 100 | 100 | 5.8 um |
| Kinl-3 (0.5 mg/ml)(ul) | 0 | 40 | 40 | 40 | 40 | 40 | 2 um |
| ATP (100 mM stock)(ul) | | | 3 | | | | 1.2 mM |
| ADP (100 mM stock)(ul) | | | | | | 3 | 1.2 mM |
| AMPPNP (100 Mm stock)(ul) | | | | | 3 | | 1.2 mM |
| Apyrase (1 unit/ul stock)(ul) | | | | 3 | | | 10 units/ml |
| 2XPEM (ul) | 100 | 100 | 100 | 100 | 100 | 100 | 1X |
| ddiH2O (ul) | 50 | 110 | 7 | 10 | 4 | 4 | |
| Total volume (ul) | 250 | 250 | 250 | 250 | 250 | 250 | |

MT = microtubules
AMPPNP Nonhydrolysable analog of ATP
Apyrase: Enzyme that hydrolyses ATP
PEM: PIPES, EDTA, MgCl2 buffer FIG. 3 shows a gel analyzing supernatants and pellets from the above assays. The tracks of the gel are numbered as in the above table. Track 3 shows an increase in tubulin in the supernatant that indicates depolymerization in the presence of ATP. No depolymerization was observed in the absence of ATP (track 4), in the presence of AMP-PNP (track 5) or in the presence of ADP (track 6).

The activity of constructs was as follows:

| Construct | ATPase activity | MT depolymerization |
|---|---|---|
| D143L546 | undetectable | no |
| E166L546 | undetectable | no |
| D183L546 | undetectable | yes |
| V195L546 | undetectable | no |
| V195S566 | undetectable | yes |

IMR90 65%: IMR90 cells harvested at 65% confluence

IMR90 Fed: IMR90 cells harvested after being confluent for 4 days

IMR90 Starved: IMR90 cells harvested after being confluent and serum starved for 4 days NT2 Undif: NT2 cells undifferentiated and proliferating NT2 Dif: NT2 cells differentiated into post-mitotic neurons Y axis: relative level of expression normalized to HeLa cells KinI-3 expression was clearly upregulated in lung, colon and breast tumors (top graphs and bottom left graph, compare the NAT bar to the adjacent CAN bar). KinI-3 expression is also correlated with the proliferation status of IMR90 and NT2 cells. When IMR90 cells are kept confluent and/or serum starved, the number of proliferating cells decreases, as does the expression level of KinI-3 (bottom right bar graph, compare IMR90 65% with IMR90 Fed and IMR90 Starved). Similarly, expression of KinI-3 is elevated in proliferating NT2 cells but dramatically decreases when these cells are fully differentiated into post-mitotic neurons (bottom right bar graph, compare NT2 Undif. with NT2 Dif.). The expression profile of KinI-3 indicates that it is involved in the cell division process.

The expression profile was also determined by end-point PCR together with cDNA dilution to generate a gross evaluation of RNA expression across 24 tissues. Plates containing the dilutions of cDNA can be obtained from Origene Technologies. KinI-3 was expressed at highest levels in the testis, was expressed at lower levels in fetal liver, the placenta, the lung, the pancreas and the adrenal gland, at lower levels in fetal brain, bone marrow, stomach, muscle, skin, prostate, lung, colon, ovary, liver, kidney, thryroid gland, heart, salivary gland, and brain, and was not detected in PBL's, small intestine or the spleen.

The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

What is claimed is:

1. An isolated nucleic acid sequence encoding a microtubule motor protein, wherein the motor protein has the following properties: (i) the protein's activity includes microtubule depolymerization activity; and (ii) the protein has a sequence that has greater than 90% amino acid sequence identity to SEQ ID NO:2 as measured using a sequence comparison algorithm.

2. An isolated nucleic acid sequence of claim 1, wherein the encoded protein specifically binds to polyclonal antibodies to a protein comprising SEQ ID NO:2.

3. An isolated nucleic acid sequence of claim 1, wherein the nucleic acid encodes SEQ ID NO:2.

4. An isolated nucleic acid sequence of claim 1, wherein the nucleic acid comprises nucleotides 840–1805 of SEQ ID NO:1.

5. An isolated nucleic acid sequence of claim 1, wherein the nucleic acid selectively hybridizes to a nucleic acid molecule of SEQ ID NO:1 in 50% (v/v) formamide, 0.1% bovine serum albumin, 0.1% Ficoll, 0.1% polyvinylpyrrolidone, 50 mM sodium phosphate buffer pH 6.5, 750 mM sodium chloride and 75 mM sodium citrate at 42° C.

6. An expression vector comprising a nucleic acid encoding a microtubule motor protein, wherein the motor protein has the following properties: (i) the protein's activity includes microtubule depolymerization activity; and (ii) the protein has a sequence that has greater than 90% amino acid sequence identity to SEQ ID NO:2 as measured using a sequence comparison algorithm.

7. A host cell transfected with the vector of claim 6.

8. The nucleic acid of claim 1, wherein the microtubule motor protein consists of amino acids 183 to 546 of SEQ ID NO:2.

9. The nucleic acid of claim 1, wherein the microtubule motor protein consists of amino acids 195–566 of SEQ ID NO:2.

10. The nucleic acid of claim 1, wherein the microtubule motor protein consists of amino acids 213–546 of SEQ ID NO:2.

11. The nucleic acid of claim 1, wherein the microtubule motor protein consists of amino acids 213–566 of SEQ ID NO:2.

12. An isolated nucleic acid sequence encoding a microtubule motor protein, wherein the motor protein has the following properties: (i) the protein's activity includes microtubule depolymerization activity; and (ii) the protein has a sequence that has greater than 90% amino acid sequence identity to SEQ ID NO:4 as measured using a sequence comparison algorithm.

* * * * *